(12) United States Patent
Wallace et al.

(10) Patent No.: US 11,096,573 B1
(45) Date of Patent: Aug. 24, 2021

(54) CORNEAL TOPOGRAPHY SYSTEM AND METHODS

(71) Applicant: Intelligent Diagnostics, LLC, Los Angeles, CA (US)

(72) Inventors: David A. Wallace, Los Angeles, CA (US); Philip Buscemi, Mount Pleasant, SC (US); Stephen D Klyce, Port Washington, NY (US); Mark A Kahan, Marlborough, MA (US); Paul E Glenn, Wellesley, MA (US); John Rogers, Monrovia, CA (US); Cesare Tanassi, Pieve di Soligo (IT); David Kramer, Torrance, CA (US); Vrunjal Mehta, Frisco, TX (US)

(73) Assignee: Intelligent Diagnostics, LLC, Los Angeles, CA (US)

( * ) Notice: Subject to any disclaimer, the term of this patent is extended or adjusted under 35 U.S.C. 154(b) by 0 days.

(21) Appl. No.: 17/045,475

(22) PCT Filed: Apr. 23, 2020

(86) PCT No.: PCT/US2020/029597
§ 371 (c)(1),
(2) Date: Oct. 5, 2020

(87) PCT Pub. No.: WO2020/219732
PCT Pub. Date: Oct. 29, 2020

Related U.S. Application Data

(60) Provisional application No. 62/977,701, filed on Feb. 17, 2020, provisional application No. 62/890,056, (Continued)

(51) Int. Cl.
*A61B 3/10* (2006.01)
*A61B 3/107* (2006.01)
(Continued)

(52) U.S. Cl.
CPC .......... *A61B 3/107* (2013.01); *A61B 3/0008* (2013.01); *A61B 3/14* (2013.01)

(58) Field of Classification Search
CPC .. A61B 3/10; A61B 3/107; A61B 3/12; A61B 3/112; A61B 3/13; A61B 3/113;
(Continued)

(56) References Cited

U.S. PATENT DOCUMENTS

| 7,130,835 B2 | 10/2006 | Cox et al. |
| 7,370,969 B2 | 5/2008 | Klyce et al. |
| (Continued) | | |

FOREIGN PATENT DOCUMENTS

| WO | WO/2018/160615 | 9/2018 |
| WO | WO/2018/167696 | 9/2018 |
| WO | WO/2019/165226 | 8/2019 |

OTHER PUBLICATIONS

International Search Report and Written Opinion of the International Searching Authority, dated Aug. 12, 2020, PCT/US20/25957, 16 pages.

*Primary Examiner* — Hung X Dang

(57) ABSTRACT

A mobile communication device-based corneal topography system includes an illumination system, an imaging system, a topography processor, an image sensor, and a mobile communication device. The illumination system is configured to generate an illumination pattern reflected off a cornea of a subject. The imaging system is coupled to an image sensor to capture an image of the reflected illumination pattern. A topography processor is coupled to the image sensor to process the image of the reflected illumination pattern. The mobile communications device includes a display, the mobile communications device is operatively coupled to the image sensor. The mobile communications device includes a mobile communications device (MCD)
(Continued)

processor. A housing at least partially encloses one or more of the illumination system, the imaging system, or the topography processor.

20 Claims, 22 Drawing Sheets

Related U.S. Application Data filed on Aug. 21, 2019, provisional application No. 62/827,801, filed on Apr. 1, 2019.

(51) Int. Cl.
*A61B 3/00* (2006.01)
*A61B 3/14* (2006.01)

(58) Field of Classification Search
CPC ......... A61B 3/14; A61B 3/0008; A61B 3/117; A61B 3/102
USPC ................ 351/206, 205, 200, 246, 221, 212
See application file for complete search history.

(56) References Cited

U.S. PATENT DOCUMENTS

| | | |
|---|---|---|
| 7,661,820 B2 | 2/2010 | Hara et al. |
| 8,545,023 B2 | 10/2013 | Holladay et al. |
| 9,078,599 B2 | 7/2015 | Yogesan et al. |
| 9,545,200 B2 | 1/2017 | Catanzariti et al. |
| 9,615,739 B2 | 4/2017 | Farrer et al. |
| 9,833,140 B2 | 12/2017 | Zhou |
| 10,129,450 B2 | 11/2018 | Nabham |
| 2006/0132711 A1 | 6/2006 | Iwanaga |
| 2009/0161090 A1* | 6/2009 | Campbell ............... A61B 3/107 356/3 |
| 2011/0299036 A1 | 12/2011 | Goldenholz |
| 2013/0286351 A1 | 10/2013 | Shimizu |
| 2016/0095752 A1 | 4/2016 | Srinivasan et al. |
| 2016/0198946 A1 | 7/2016 | Zhou |
| 2017/0042421 A1 | 2/2017 | Wallace et al. |
| 2017/0357879 A1 | 12/2017 | Odaibo et al. |
| 2018/0000339 A1 | 1/2018 | Hipsley |
| 2018/0125355 A1 | 5/2018 | Mrochen et al. |
| 2018/0249905 A1 | 9/2018 | Farrer et al. |

* cited by examiner

CORNEAL TOPOGRAPHY SYSTEM AND METHODS

RELATED APPLICATIONS

This application claims priority to PCT Application No. PCT/US2020/25957, filed Mar. 31, 2020, entitled "Corneal Topography Systems and Methods," U.S. provisional patent application Ser. No. 62/977,701, filed Feb. 17, 2020, entitled "Corneal Topography System and Methods; U.S. provisional patent application Ser. No. 62/890,056, filed Aug. 21, 2019, entitled "Mobile Communication Device-Based Corneal Topography System Improvements,"; and U.S. provisional patent application Ser. No. 62/827,801, filed Apr. 1, 2019, entitled "Improvements in a Mobile Communication Device-Based Corneal Topography System," the entire disclosures and content of which are all hereby incorporated by reference.

BACKGROUND

Prior art corneal topography systems (which may be connected to a laptop computer or a desktop computer) project an image of Placido rings off of a cornea of a human eye and into a digital imaging sensor (or one or more digital imaging sensors). Some prior art systems are affixed to a desktop computer or may attach to a laptop computer, each of which may be typically running a Windows operating system or a MAC operating system. Prior art desktop-based or laptop-based corneal topography systems may use an image sensor and a custom, proprietary imaging lens system designed to suit the desired parameters of the instrument including field of view, focal length, and desired image magnification to maximize use of the target commercial image sensor for its intended purpose.

A prior art corneal topography system attached to a smartphone is described in "An Accessible Approach to Corneal Topography" by Andre Luis Beling da Rosa ("Beling da Rosa publication") in December of 2013. The article describes a clip-on device with three layers: 1) an illumination layer to provide illumination of concentric rings; 2) a support layer helping with the image captured using a lens and also with the diffusion and 3) the pattern layer (which gives a shape to projected patterns). A smartphone clip-on device having three layers according to the prior art as shown in pages 40 and 41 of the Beling da Rosa publication. However, this device was described as part of a PhD thesis for a computer-science degree and was never commercialized. Another prior art corneal topography system attached to a smartphone is described in "Design And Development Of An Ultraportable Corneal Topographer For Smartphones As A Low Cost New Tool For Preventing Blindness Caused By Keratoconus" by Pinheiro et al ("Pinheiro publication"). This device includes a support cover, a printed circuit board with LEDs (light emitting diodes), an optical system for magnification, a cone with transparent and black concentric rings (principle of Placido) and a dome. However, the Pinheiro publication does not describe any details of an optical system. The Pinheiro publication device did not appear to have a system to confirm vertex distance, so the device cannot internally calibrate. In at least some instances with previous systems, an operator had to manually determine when the correct vertex distance was reached. In these previous systems, the operator could make mistakes and this resulted in poor image quality or unfocused captured Placido rings (or other image pattern) images.

A need exists for a smartphone corneal topography system that is cost effective for a medical professional.

SUMMARY

In some embodiments, a mobile communication device-based corneal topography system includes an illumination system configured to generate an illumination pattern reflected off a cornea of a subject; an imaging system coupled to an image sensor to capture an image of the reflected illumination pattern; a topography processor operatively coupled to the image sensor to process the image of the reflected illumination pattern and a mobile communications device, the mobile communications device including a display. The mobile communication device may be operatively coupled to the image sensor, the mobile communications device comprising a mobile communications device (MCD) processor. In some embodiments, a housing may at least partially enclose one or more of the illumination system, the imaging system, or the topography processor.

In some embodiments, a mobile communication device-based corneal topography system may include a mobile communication device comprising a mobile communication device (MCD) processor and a display; a fixation beam source to generate a fixation beam and direct the fixation beam to the cornea of the subject, the fixation beam defining a fixation target visible to the eye of the subject, the fixation target beam comprising a first wavelength of light; a ranging beam source to generate a ranging beam and direct the ranging beam to a cornea of a subject, the ranging beam comprising a second wavelength of light different from the first wavelength of light; an imaging system coupled to an image sensor to capture a reflected image of the ranging beam and the fixation beam on the cornea; and a topography processor. In some embodiments, the topography processor may be operatively coupled to the image sensor and configured with instructions to: determine when the ranging beam and the fixation beam are overlapping by tracking the first wavelength of light and the second wavelength of light with spectral analysis and determining the fixation beam and the ranging beam are aligned with a mark in a center of the reflected image; turn off the ranging beam source and the fixation beam source; automatically capture, at the image sensor, an image of a reflected illumination pattern reflected off the cornea of the subject; transmit the captured image of the reflected illumination pattern to the topography processor; and process, by the topography processor, the image of the reflected illumination pattern to generate topography map images and one or more topography data files.

In some embodiments, an auto-capture method for use in corneal topography systems may include capturing, at an image sensor, a reflected image of a fixation beam at a first wavelength of light and a ranging beam at a second wavelength of light on a cornea; communicating the reflected image of the fixation beam and the ranging beam to the topography processor; communicating the reflected image of the fixation beam and the ranging beam to a mobile communication device for display; spectrally analyzing, by the topography processor, the first wavelength of light and the second wavelength of light to determine whether the fixation beam and the ranging beam are overlapping; determining that a fiducial mark in a center of the reflected image is aligned with the fixation beam and the ranging beam; communicating instructions to turn off the ranging beam and the fixation beam; and automatically capturing, at the image sensor, an image of an illumination pattern reflected off the cornea of the subject.

In some embodiments, a system may calculate eye pupil measurements, including a first lens assembly having a rear surface and a front surface; a second lens assembly; a fixation light source to generate a fixation light beam, wherein the fixation light beam is transmitted through the first lens assembly and the second lens assembly to a patient's cornea; and an infrared light source to generate an infrared light beam. In some embodiments, the infrared light beam is reflected off the front surface of the first lens assembly and transmitted through the second lens assembly to the patient's cornea. In some embodiments, the infrared light beam and the fixation light beam are introduced on-axis to the patient's eye to be utilized in calculate eye pupil measurements.

In some embodiments, a mobile communication device-based corneal topography system may include a custom-designed mobile communication device, the custom-designed communication device may include a display, one or more memory devices, one or more processors and/or computer-readable instructions stored in the one or more memory devices, the computer-readable instructions including a custom-designed and developed operating system to control operations of components of the custom-designed mobile communication device. In some embodiments, a corneal topography system or housing, the corneal topography system or housing including one or more memory devices, one or more processors and/or computer-readable instructions stored in the one or more memory devices, the computer-readable instructions also including the custom-designed and developed operating system to control operations of components of the corneal topography system or housing.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the features, advantages and principles of the present disclosure will be obtained by reference to the following detailed description that sets forth illustrative embodiments, and the accompanying drawings of which.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Figure 4A:
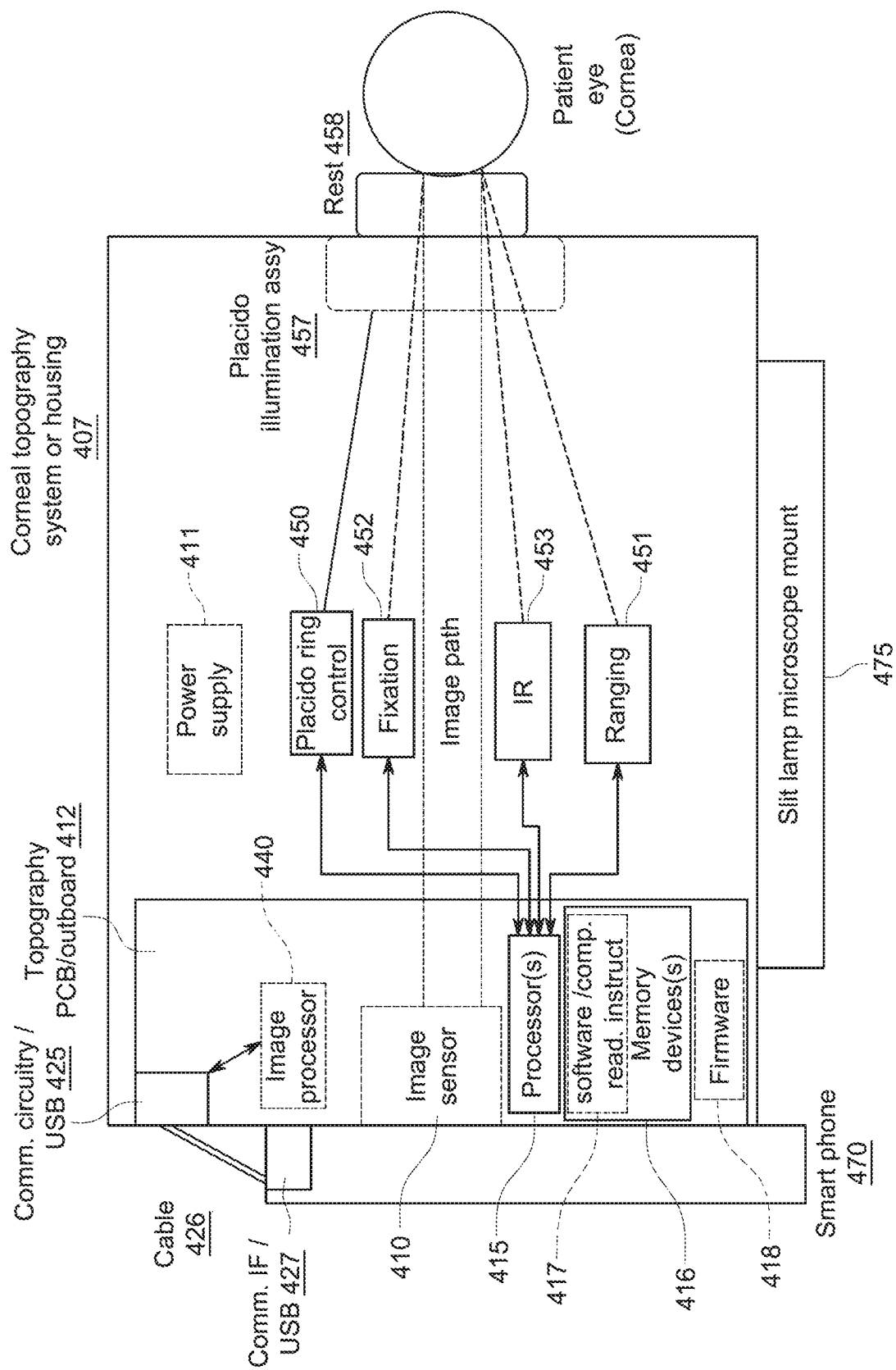
FIG. 4A illustrates a block diagram of corneal topography system including system components for corneal topography at least partially contained within a housing (including a camera sensor) according to some embodiments.
Figure 5:
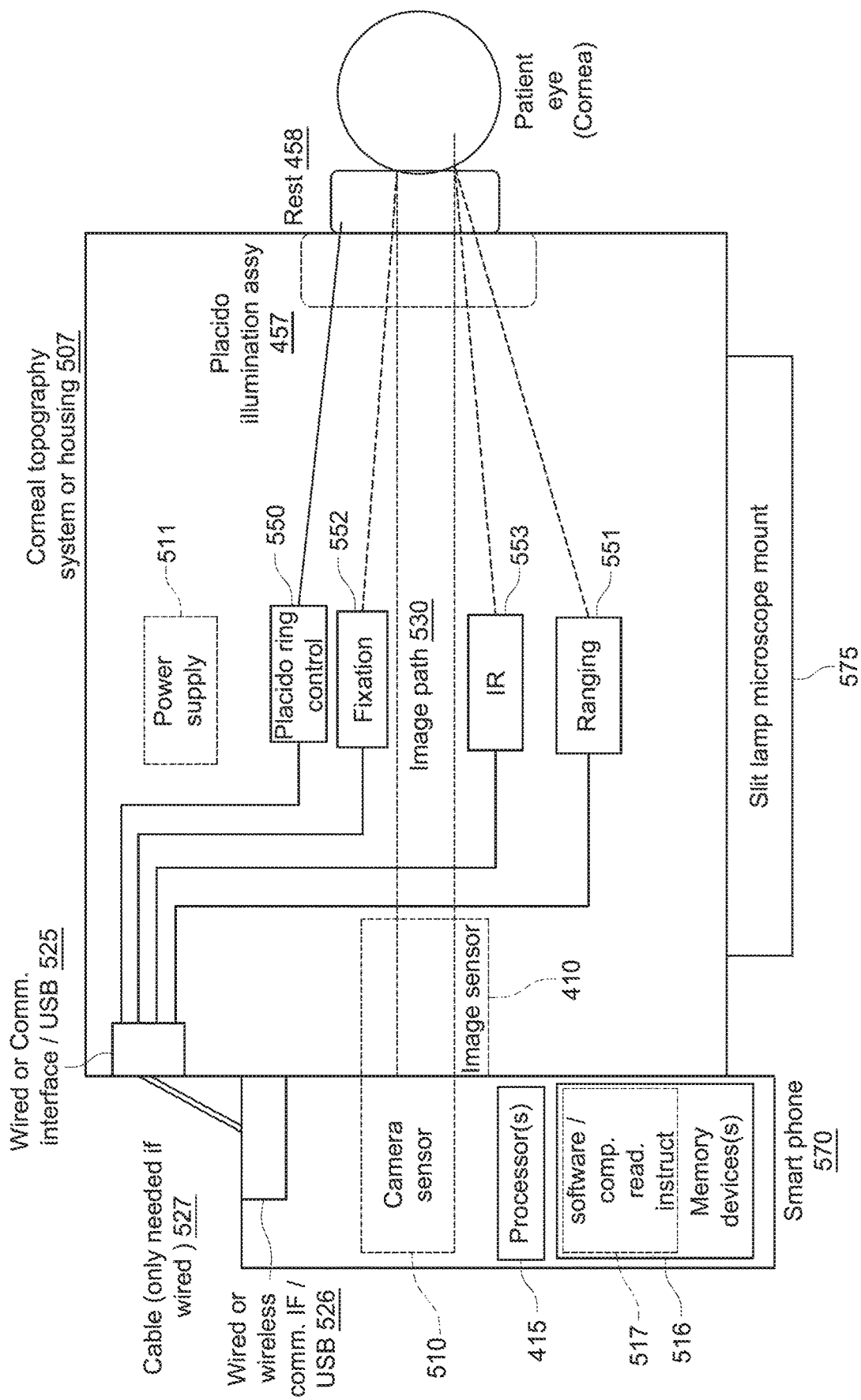
FIG. 5 illustrates an alternative embodiment utilizing a custom-designed and developed mobile communications device according to some embodiments.

FIG. 4A describes an embodiment where an image sensor or a camera sensor may be included or partially included as part of the corneal topography system or housing (containing the Keplerian telescope lenses and/or beam folding mirrors) while residing on a custom-designed outboard printed circuit board (PCB). In these embodiments the corneal topography software may be stored in memory devices (e.g., ROM, firmware and/or non-volatile memory) and the image sensor or camera sensor may be included on the topography-specific outboard PCB. In some embodiments, the mobile communication device is custom designed to use in the corneal topography system and the operating system of the mobile communication device is also a specific and custom designed to be maximally compatible with the corneal topography system. FIG. 5 illustrates an embodiment where the mobile communication device's camera may be utilized to capture the Placido rings image reflected off of the cornea, the topography (and image processing) software may be stored and executed on the mobile communication device and where the mobile communication device (and operating system) may be a custom-designed and fabricated to be used in the mobile communication device-based corneal topography system.

Figure 1A:
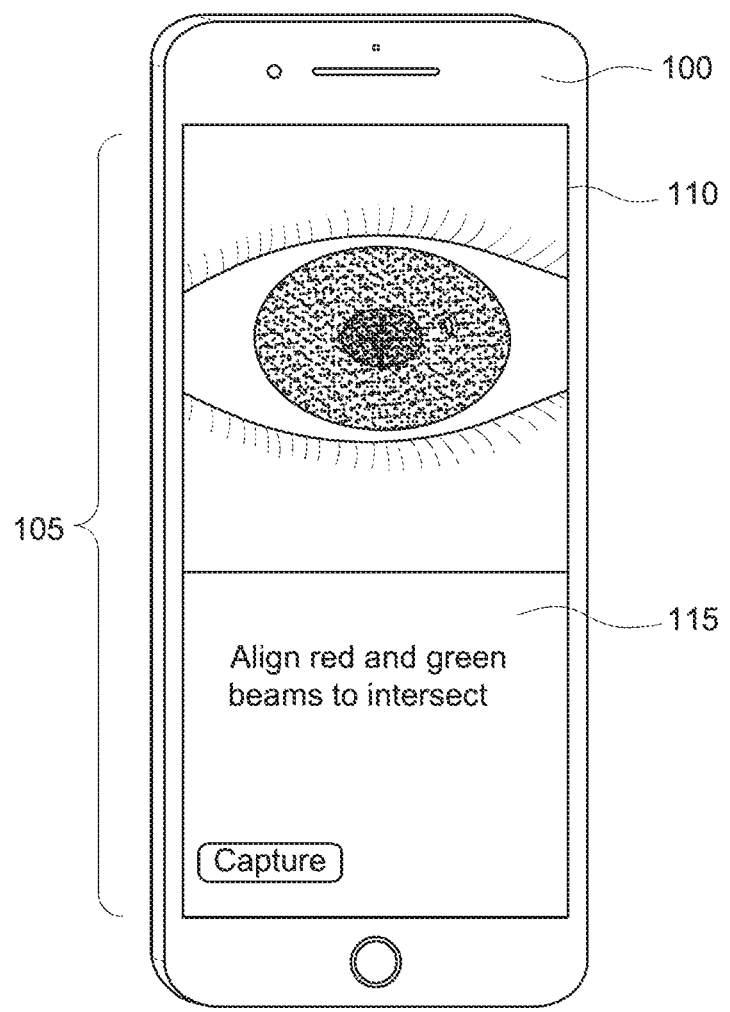
FIG. 1A illustrates a mobile communications device running a corneal topography software application according to some embodiments.
Figure 1B:
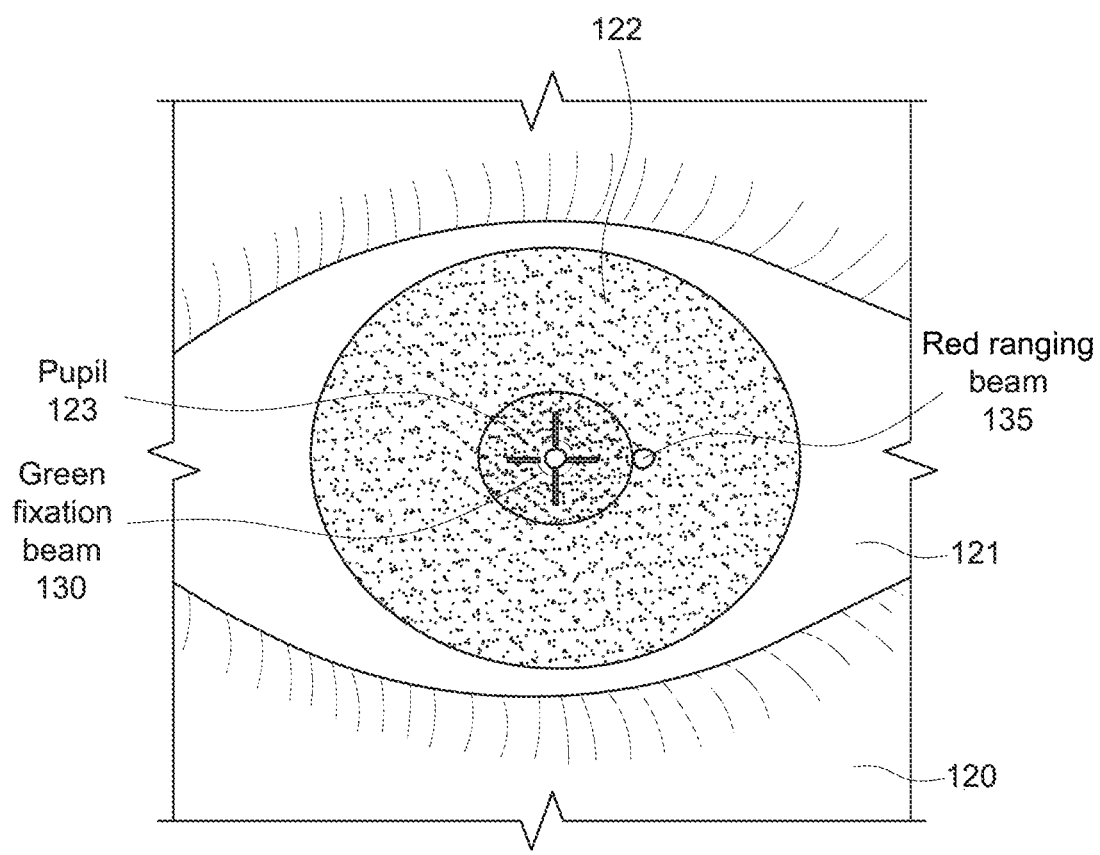
FIG. 1B illustrates a screen of the corneal topography software application when a red ranging beam is not intersecting with a reflection from a green fixation beam according to some embodiments.
Figure 1C:
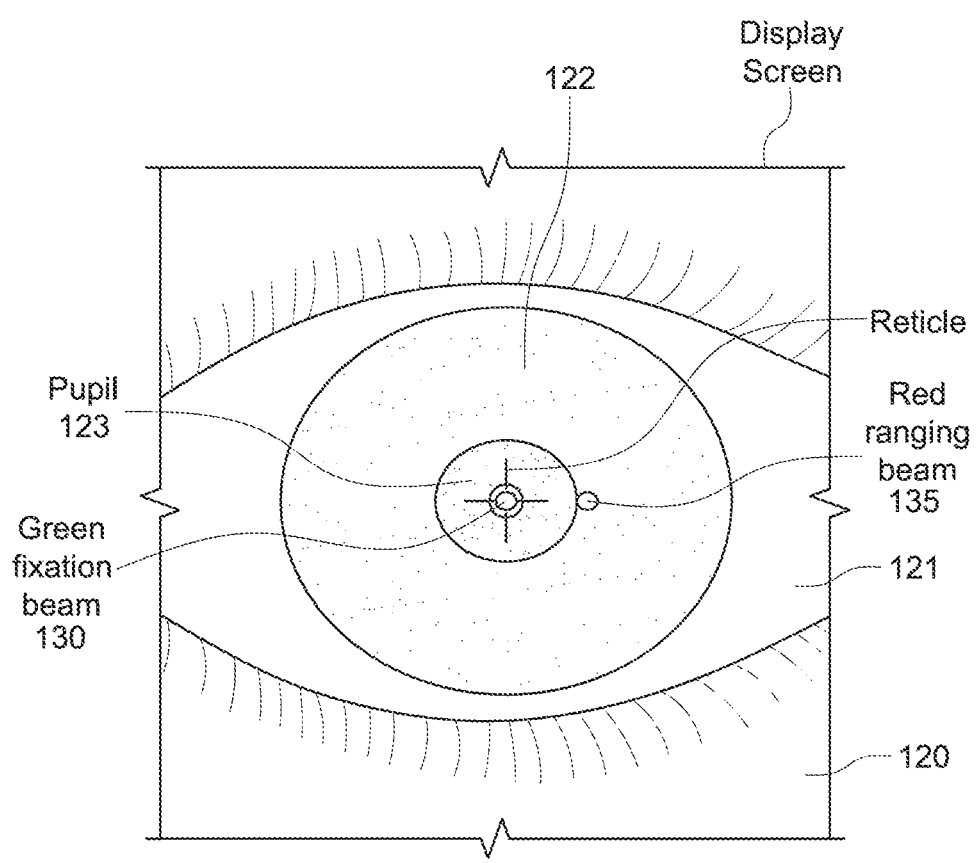
FIG. 1C is an illustration of a display screen showing a red ranging beam and a green fixation beam that have been activated and are seen on a video image of the patient's cornea according to some embodiments.
Figure 1D:
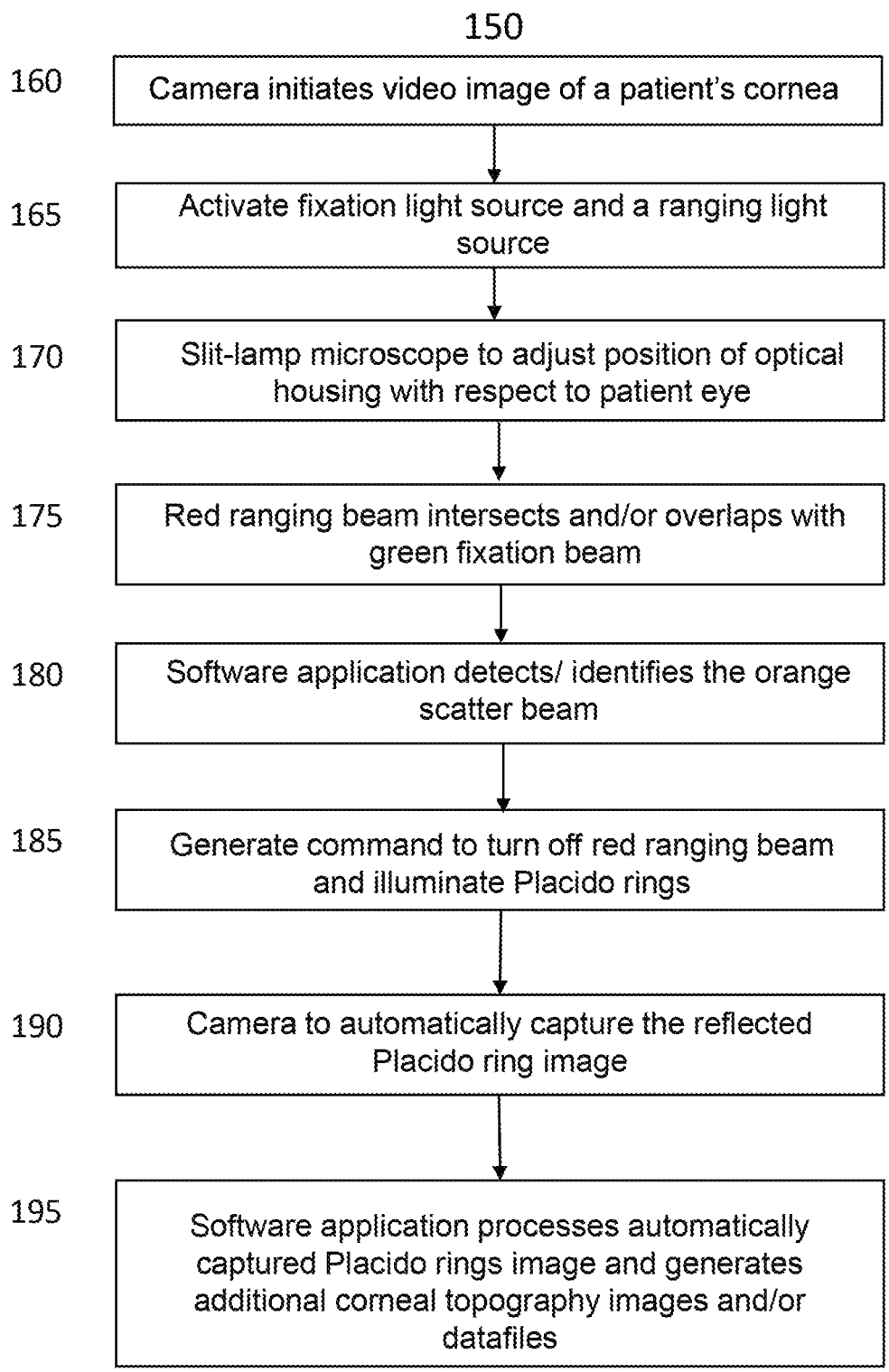
FIG. 1D illustrates a flowchart for the auto-capture process according to some embodiments.
Figure 2:
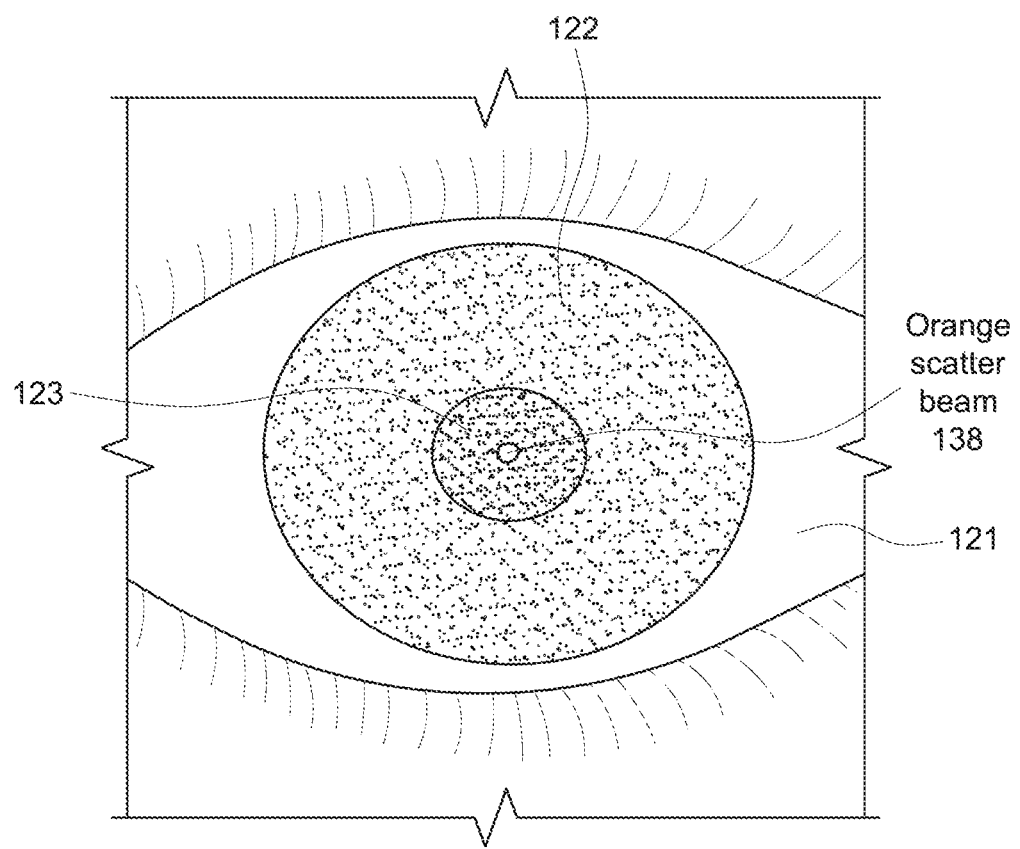
FIG. 2 illustrates a screen of the corneal topography software application when the red ranging beam and the green fixation beam intersect or overlap according to some embodiments.
Figure 2A:
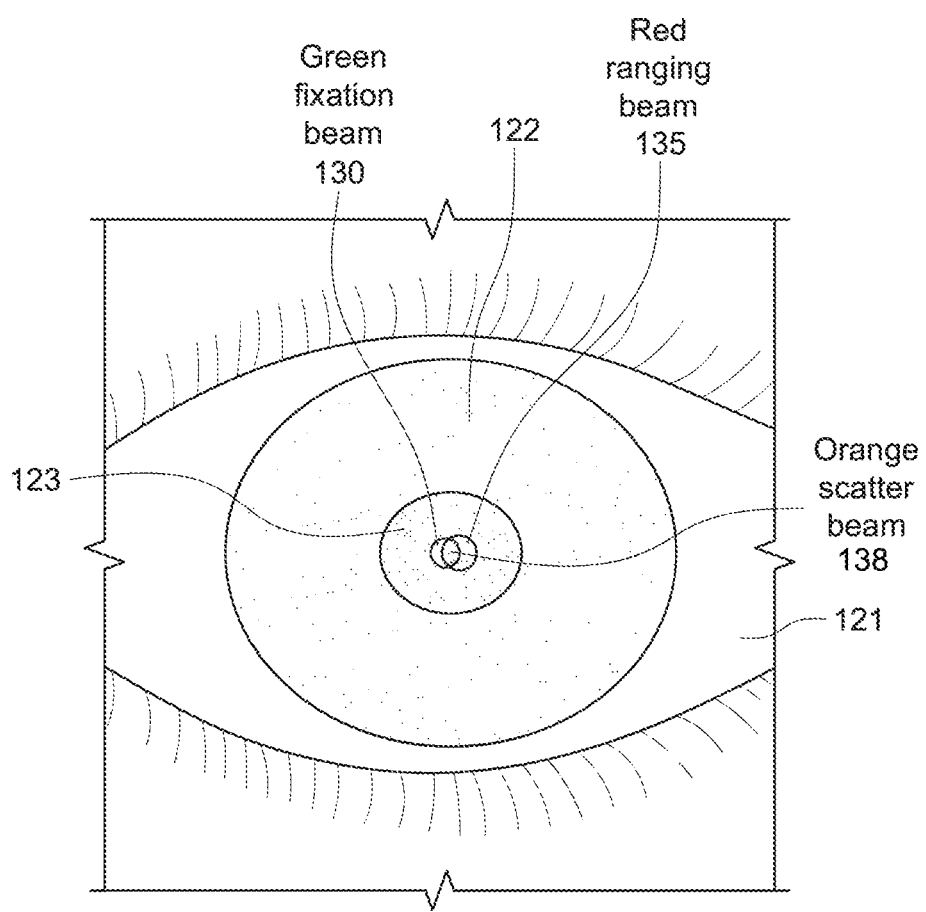
FIG. 2A illustrates a screen of the corneal topography software application when the red ranging beam and the green fixation beam intersect so as to overlap and produce an orange scatter beam according to some embodiments.
Figure 2B:
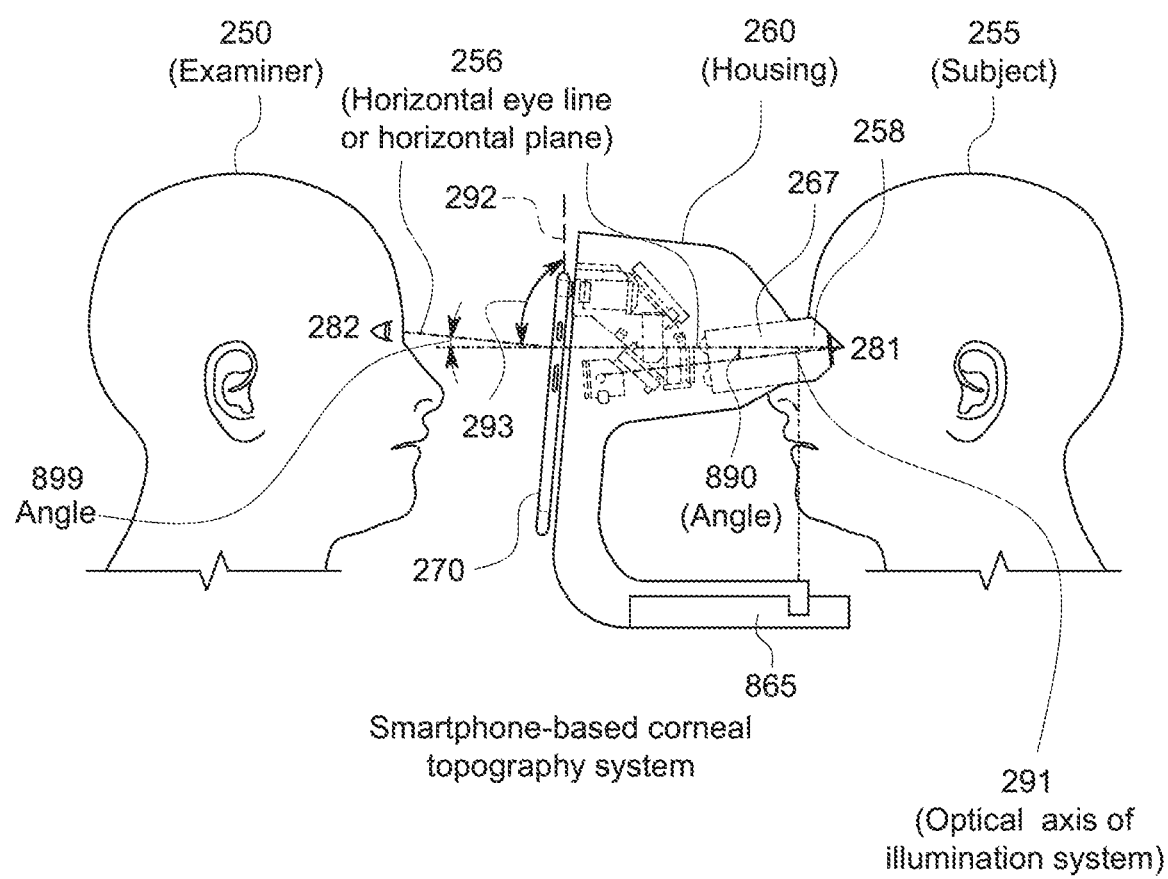
FIG. 2B illustrates a side view of a patient being examined by an examiner utilizing a mobile communication device-based corneal topography system according to some embodiments.

FIGS. 1A, 1B, 1C, 1D and FIGS. 2, 2A, 2B, 2C, 2D and 2E describe an auto-capture process according to some embodiments that may be utilized in the embodiments described above of the mobile communication device-based corneal topography system. FIG. 3 describes an infrared illumination system utilized for pupil edge detection according to some embodiments that may be utilized in the embodiments described above of the mobile communication device-based corneal topography system.

This patent application begins with the description of the auto-capture process and follows with a description of the infrared illumination system. In some embodiments, a mobile communication device-based corneal topography system may comprise a mobile communication device and a corneal topography system or housing. The corneal topography system may also be referred to as a corneal topography optical bench or a corneal topography housing in this disclosure. In some embodiments, the corneal topography system may be mounted onto a post of a slit-lamp microscope to allow adjustment in positioning of the mobile communication device-based corneal topography system with respect to the patient being examined in an x-direction, a y-direction and a z-direction. In some embodiments, the z-direction may be moving the corneal topography system closer or farther from a patient being examined (e.g., movement in a forward or a backward direction). In some embodiments, the x-direction may be moving the corneal topography system in a left or right direction with respect to the patient being examined. In some embodiments, the y-direction may be moving the corneal topography system in a up or down direction with respect to the patient being examined.

In some embodiments, the mobile communication device may comprise one or more processors, a display screen, one or more memory devices and computer-readable instructions stored and/or resident on the memory devices. In some embodiments, the computer-readable instructions may be accessed and executable by the one or more processors of the mobile communication device to initiate and execute a corneal topography smartphone software application. In this embodiment, the mobile communication device may further communicate with one or external server computing devices (e.g., cloud-based servers) utilizing wireless communication transceivers such as Wi-Fi transceivers, personal area network transceivers, and/or other wireless cellular transceivers. These operations are previously described in the U.S. patent and patent applications referenced above.

FIGS. 1A to 1D describe operation of the auto-capture process according to some embodiments. In some embodiments, the corneal topography application software (the corneal topography app) is resident on the smartphone. In some embodiments, the corneal topography application software may be stored in one or more memory devices of the mobile communication device and a remainder of the corneal topography software may be stored in one or more memory devices of the corneal topography system. In some embodiments, one or more memory devices may be within the housing of the corneal topography system (e.g., on the topography-specific PCB or outboard). In some embodiments, all of the corneal topography software is not stored in the one or more memory devices of the corneal topography system because the mobile communication device has at least the user interface software of the application software as well as other software components in order to interface with the corneal topography system.

In some embodiments, a mobile communications device-based corneal topography system is configured for the corneal topography software to automatically capture a Placido rings image (or an image pattern) reflected off a patient's cornea when the mobile communication device (or image sensor) and the patient's eye are at the correct vertex distance with respect to each other.

FIG. 1A illustrates a mobile communications device running a corneal topography smartphone software application according to some embodiments. FIG. 1B illustrates a screen of the corneal topography software application when a red ranging beam is not intersecting with a green fixation beam according to some embodiments. Figure1C illustrates a display screen of the corneal topography software application when a red ranging beam is not intersecting with a green fixation beam according to some embodiments. FIG. 1D illustrates a flowchart for the auto-capture process according to some embodiments. FIG. 2 illustrates a screen of the corneal topography software application when the red ranging beam and the green fixation beam intersect or overlap and produce an orange scatter beam according to some embodiments. FIG. 2A illustrates a screen of the corneal topography software application when the red ranging beam and the green fixation beam intersect or overlap and produce an orange scatter beam according to some embodiments. FIG. 2B illustrates a side view of a patient being examined by an examiner utilizing a mobile communication device-based corneal topography system according to some embodiments.

In some embodiments, the corneal topography smartphone application may be initiated or started. In some embodiments, an image sensor in the corneal topography system may initiate display of video images 110 of a patient's cornea which may be communicated to the mobile communication device and presented on a mobile communication device display (e.g., such as the corneal image displayed in FIG. 1A). In some embodiments, a communication interface in the corneal topography optical system or housing may communicate the obtained video corneal image to the mobile communication device (e.g., the corneal topography software application executing on the mobile communication device). In other embodiments, a wireless communication interface may communicatively couple and/or connect the corneal topography system or housing to the mobile communication device. As illustrated in FIG. 1A, in some embodiments, the mobile communication device 100 may include a display screen 105. In some embodiments, the corneal topography application software may include a screen or menu showing video images 110 of a patient's eye, including the iris, the pupil, the cornea and a lower section of the screen or menu 115 where commands and text may be displayed or other menu items may be displayed.

FIG. 1D illustrates a flowchart for the auto-capture process 150 according to some embodiments. At a step 160, a camera initiates video image capture of a patient's cornea. At a step 165, a fixation light source and a ranging light source are activated. At a step 170, a slit-lamp microscope is adjusted to position an optical housing with respect to a patient's eye. At a step 175 a ranging beam such as a red ranging beam intersects and/or overlaps with a fixation beam such as a green fixation beam. At a step 180, a software application detects and/or identifies the overlap of the of the ranging beam and the fixation beam. At a step 185, a command is generated to turn of the ranging beam and illuminate the cornea with a pattern such Placido rings. At a step 190, a camera automatically captures one or more images the reflected pattern such as Placido rings. At a step 195, a software application processes the captured one or more images.

Although FIG. 1D shows a method in accordance with some embodiments, a person of ordinary skill in the art will recognize many adaptations and variations. For example, some the steps can be repeated, some of the steps omitted, and the steps can be performed in any suitable order. Some of the steps may be performed sequentially, and some of the steps may be performed at substantially the same time, e.g. simultaneously. In some embodiments, as illustrated in FIG. 1D, at step 165, a fixation light source and/or a ranging light source in the corneal topography system may be activated. In some embodiments, the corneal topography smartphone software application may communicate with the light sources (e.g., the ranging light source and the fixation light source) in the corneal topography system or housing via the wired communication interface (e.g., a USB communication interface) to turn on the fixation light source and/or the ranging light source. Alternatively, a corneal topography smartphone application may communicate with a corneal topography system or housing utilizing a wireless communications protocol and interface (e.g., such as Bluetooth or Zigbee or WiFi or Near Field Communications (NFC)). In some embodiments, an operator or user may utilize controls (e.g., switch(es) or button(s)) on the corneal topography system or housing to activate the light sources (e.g., the ranging light source and the fixation light source).

In some embodiments, a fixation light source may be a green LED and may generate a green light beam, although the fixation light source may emit light of any visible wavelength or combination of wavelengths. In some embodiments, for example, a fixation light source may be a green LED assembly. In some embodiments, a fixation light source may have a wavelength of approximately 525 nanometers (+/−15 nm). In some embodiments, a fixation light source may be an OSRAM LT T64G-DAFA-29-0-20-R33-Z. In some embodiments, a ranging light source may be a red LED or laser and may generate a red laser beam. In some embodiments, a ranging light source may be a red laser having a wavelength of 650 nm (+/−15 nm). In some embodiments, a ranging laser may be a Laserlands 3.5 mW 650 nm Red Laser Dot Module. Although reference is made to a red ranging light source, the ranging light source may comprise any suitable wavelength, such as visible, ultraviolet, infrared or near infrared light. In other embodiments, other light sources having different wavelengths may be utilized as long as the light beam utilized for the fixation beam and the light beam utilized for the ranging light beam may be distinguished from each other. Alternatively, light of similar wavelengths may be used, and the ranging light beam tracked with the application software until the ranging light beam overlaps with the reflection of the fixation light.

FIG. 1B illustrates a video image of a patient's eye when a green fixation beam and a red ranging beam are activated and projected onto a patient's cornea. In some embodiments, as is shown in FIG. 1B, the green fixation beam 130 may be directed to a center portion of a pupil 123 of the eye because the patient may be focusing on the fixation light source (e.g., green light source). In some embodiments, the menu display of the video cornea image may also display a patient's eye 120, a white scleral portion 121 of a patient's eye, an iris 122 of a patient's eye and a pupil 123 of a patient's eye. In some embodiments, the red ranging beam 135 may be angled towards the patient's cornea (e.g., may be transmitted to the patient's cornea at a 45 degree angle). In some embodiments, the red ranging beam 135 may be directed towards the patient's eye at an angle of 30 to 60 degrees with respect to a front surface of the patient's cornea. FIG. 1B illustrates an embodiment when alignment a correct vertex distance to the corneal topography system has not yet been achieved, but the green fixation beam 130 and the red ranging beam 135 have both been activated and are transmitted to a patient's cornea and are seen on the video image of the patient's cornea. FIG. 1C illustrates an embodiment when a correct vertex has not yet been achieved, but the green fixation beam 130 and the red ranging beam 135 have both been activated and are transmitted to a patient's cornea and are seen on the video image of the patient's cornea along with a computer generated marker such as a reticle. In some embodiments, the green fixation beam 130 may be at a center or near a center of the pupil 123 in the video image. In some embodiments, the red ranging beam 135 may not yet be inside the pupil 123 in the video image. In some embodiments, the reticle may be positioned in the video image of the patient's pupil 123. FIG. 1C is an illustration of a display screen showing a red ranging beam and a green fixation beam have been activated and are seen on a video image of the patient's cornea according to some embodiments.

In some embodiments, an operator or medical professional may move at step 170 a slit-lamp microscope in an x-direction, a y-direction or a z-direction. In some embodiments, in moving the slit-lamp microscope in a z-direction, the operator or medical professional may be attempting to determine or locate an ideal or correct vertex distance from an image sensor or from a mobile communication device to the patient's cornea in order to generate a focused image of the Purkinje image reflected from the patient's cornea. In some embodiments, the x-axis may be a horizontal axis, the y-axis may be a vertical axis and the z-axis may be a distance from an image sensor or a mobile communication device's correct focal plane to the corneal vertex.

In some embodiments, as the slit-lamp microscope is moved (e.g., in a z-axis direction), the red ranging beam 135 may intersect, overlap, or be superimposed at step 175 with the green fixation beam 130 on a video image of a patient's cornea at a desired vertex distance. In some embodiments, an intersection of the green light beam and the red light beam may produce an orange scatter light on the patient's cornea which can be viewed or seen in the video image of the patient's cornea. In some embodiments, the perceived orange scatter light comprises scattered light from the red ranging beam and reflected light from the green fixation beam, corresponding to a region of overlap. FIGS. 2 and 2A illustrate when the red ranging beam intersects with the green fixation beam and produces an orange scatter beam 138 on a video image of the patient's cornea. In this embodiment, the red ranging beam intersects the green fixation beam to produce the orange scatter beam 138 on the video image of the patient's cornea. In some embodiments, a size of an orange scatter beam 138 may not be larger than a size of the either the red ranging beam and/or the green fixation beam because the orange scatter beam is identifying when there is an intersection of the two beams (e.g., the intersection of ranging beam and fixation beam).

In some embodiments, the corneal topography software (or a combination of hardware and/or software) may detect or identify at step 180 the orange scatter beam on the displayed corneal video image. In other words, computer-readable instructions may be executable by one or more processors on a topography-specific outboard or PCB in a corneal topography system to determine when an orange scatter beam 138 is present on the displayed patient corneal video image (which identifies that the mobile communication device or the corneal topography image sensor may be at the correct vertex distance from the patient's cornea). Although reference is made to an orange scatter beam, the instructions can be configured to detect overlap the reflected fixation beam and the scattered ranging beam with any combination of wavelengths as described herein.

In some embodiments, at step 185 the corneal topography software application may cause the mobile communication device to generate an instruction, signal or command to turn off or deactivate the red ranging beam 135 in the corneal topography system and to illuminate an illumination pattern in an illumination system (e.g., Placido rings in the Placido ring illumination system). In some embodiments, an illumination pattern may be reflected onto a patient's cornea. In some embodiments, a Placido rings image may be reflected onto a patient's cornea. In some embodiments, the red ranging beam may be turned off so as to not interfere with the reflection of the illumination pattern (e.g., the Placido rings) on the patient's cornea. In some embodiments, the illumination pattern (e.g., the Placido rings pattern) may be illuminated at the same time that the green fixation beam and the red ranging beam are activated in the corneal topography system. This may be possible because the luminance value may not be high in the mobile communication device-based corneal topography system. In other words, in some embodiments, the intersection or overlap of the green fixation beam with the red ranging beam (e.g., the produced orange scatter beam) may be detected even if the illumination pattern is turned on (e.g., the Placido rings are illuminated).

In some embodiments, the corneal topography software application may wait a predetermined time after the corneal topography software application determined that the red ranging light beam 135 has overlapped (or intersected or is superimposed) with the green fixation light beam 130 in the video image of the patient's cornea. In some embodiments, the corneal topography software application may be verifying that the overlapping or intersection is a continuous or stable occurrence and is not just an artifact or a temporary or fleeting intersection, overlapping, or superimposing of the red ranging beam with the green fixation beam in the video cornea image. In these embodiments, this provides additional verification that the correct vertex distance may be present.

In some embodiments, the corneal topography software application may verify that the intersection of fixation light beam and the ranging light beam occurs for a number of corneal image video frames before automatically capturing a reflected illuminated pattern image (e.g., Placido rings image) of a patient's cornea. In this embodiment, the corneal topography software application may verify that a predetermined number of video frames have this intersection or overlapping of the green fixation beam and the red ranging beam in order to verify that the patient or the corneal topography system (e.g., the corneal topography optical bench) is not moving and stability has been achieved. In some embodiments, the movement that is being referred to is the movement of the patient's eye relative to the corneal topography system or housing. In some embodiments, two or more successive corneal video images may be stored in a memory buffers (which may be circular or linear memory buffers, or a circular video buffer) and the corneal topography software application may verify that superimposition or overlapping occurs in these two or more video images (e.g., that the orange scatter beam is present in the two or more corneal video images).

Although reference is made to the ranging beam overlapping with the fixation beam in the image, in some embodiments, the processor instructions are configured to initiate the illumination pattern and image capture when the fixation beam and the ranging beam are sufficiently close in the image and not yet overlapping.

At a step 190, the camera automatically captures the image of the pattern reflected from the cornea, e.g. the Placido rings.

In some embodiments, the corneal topography software application may process at step 195 the automatically captured illuminated pattern image (e.g., Placido rings image) and further generate additional related corneal topography images (e.g., a Placido ring edge detection image) and/or datafiles. For example, the corneal topography software application may generate a corneal topography power map and/or a patient's corneal topography data file. In some embodiments, the corneal topography software functionality may be performed in the corneal topography system or housing (e.g., by computer-readable instructions executable by one or more processors of the corneal topography system), and the resulting images and related parameters may be communicated or transmitted, via the communication interface or communication circuitry to the mobile communication device, and the resulting images may be generated and presented on the display of the mobile communication device.

Although the description above identifies that the functions of the corneal topography software may be performed by components partially contained within the corneal topography system (e.g., by computer-readable instructions executable the one or more processors), in some embodiments, some components or modules of the corneal topography software functionality may be performed on the mobile communications device and the resulting images may be communicated and/or transmitted to a cloud-based server. In some embodiments, the corneal topography software of the corneal topography system may only capture the reflected illuminated pattern image (e.g., Placido rings image) and the additional corneal topography image processing may be performed on a cloud-based server (after the reflected illuminated pattern image (e.g., Placido rings image) has been communicated to the mobile communication device and then to the cloud-based server). As will be discussed with respect to FIG. 4A, corneal topography software stored in the one or more memory devices of the corneal topography system or housing may perform the automatic capture of the reflected Placido rings image as well as perform the resulting corneal topography image processing (e.g., generating a Placido ring edge detection image, one or more patient data files and/or corneal topography power map) in order to reduce the processing requirements on the mobile communication device and/or also to maintain tighter control of the mobile communication device-based corneal topography system (e.g., there is no need to worry about changes in the mobile computing device software or drivers which could cause problems with the corneal topography system).

While the above disclosure specifies a green fixation light beam, a red ranging light beam and an orange scatter beam, the embodiments disclosed herein are not limited to these color light beams and/or wavelengths. Different color light beams or wavelengths may be utilized for the fixation light beam and different color light beams or wavelengths may be utilized for the ranging light beam. In some embodiments, one qualification would be that a color of the fixation light beam has to be a different color or wavelength than a color or wavelength of the ranging light beam in order for a user, operator, software or system to be able to detect when the fixation light beam and the red ranging beam are overlapping or intersecting. In some embodiments, the color or wavelength selected for the ranging light beam and the color or wavelength selected for the fixation light beam may have to be visible in the video display on the mobile communication device in order for the user, operator or software to detect its presence. In other words, the color or wavelength of the fixation light beam and/or the ranging light beam could not be a same color as the subject's iris or pupil. In some embodiments, the light-scatter beam may be the additive result of the selected fixation light beam color or wavelength and the selected ranging light beam color or wavelength. For example, in some embodiments, if the ranging light beam was a blue light beam and the fixation light beam was a red light beam, the light-scatter beam created by the intersection or overlapping of the ranging light beam and the fixation light beam may be purple light scatter, although the claimed subject matter is not limited to the above-described example. In some embodiments, the light scatter triggering auto-capture would be analyzing the video image to identify when the light scatter beam is the additive color of the ranging light beam and the fixation light beam.

In some embodiments, the ranging beam may be referred to as an alignment beam. In some embodiments, the image sensor may be referred to as a camera sensor or a detector. In some embodiments, a system including auto-capture may comprise a fixation target beam, an alignment beam, a detector, and a processor coupled to the detector. In some embodiments, the illumination pattern may be reflected from the cornea. In some embodiments, the fixation target beam may define a target visible to an eye and the fixation target beam may comprise a first wavelength of light. In some embodiments, the alignment beam may be focused to a beam waist at a location overlapping with the fixed target beam, the alignment beam comprising a second wavelength of light different from the first wavelength of light. In some embodiments, the detector may image or capture an image of the reflection of the target beam and the alignment beam from the cornea. In some embodiments, the processor may be coupled to a detector and the processor may be configured with instructions to display an image of the eye with a portion of the image showing the fixation beam overlapping with the alignment beam. In some embodiments, the processor may be configured with instructions to illuminate the illumination pattern and capture an image of the illumination pattern reflected from an anterior surface of the cornea in response to a reflection of the fixation beam overlapping the alignment beam.

In some embodiments, the alignment beam may be configured to overlap with the fixation beam at a vertex of the cornea. In some embodiments, the fixation beam may comprise substantially collimated light prior to reflection from the cornea. In some embodiments, the image of the fixation beam from an anterior surface of the cornea comprises a maximum size across within a range from about 10 um to about 1 mm. In some embodiments, the fixation beam may be collimated to within about 45 degrees. In some embodiments, the alignment beam may be focused to the waist at a full cone angle within a range from about 1 degree to 45 degrees.

In some embodiments, the detector may comprise an array of pixels, and the array of pixels may comprise a first plurality of pixels more sensitive to the first wavelength than the second wavelength and a second plurality of pixels more sensitive to the second wavelength than the first wavelength. In some embodiments, the first wavelength comprises a first color and the second wavelength comprise a second color different from the first color. In some embodiments, the processor may be configured with instructions to display a portion where the first beam overlaps with the second beam with a different color than the first wavelength and the second wavelength. In some embodiments, the image of the alignment beam may comprise an image of scattered life from the cornea when a tear fil covers the cornea. In some embodiments, the scatter light may comprise light scattered from a Bowman's membrane or a stroma of the eye beneath a tear film of the eye. In some embodiments, the alignment beam may extend along an alignment beam axis at an oblique angle to an axis of the fixation beam.

Figure 2C:
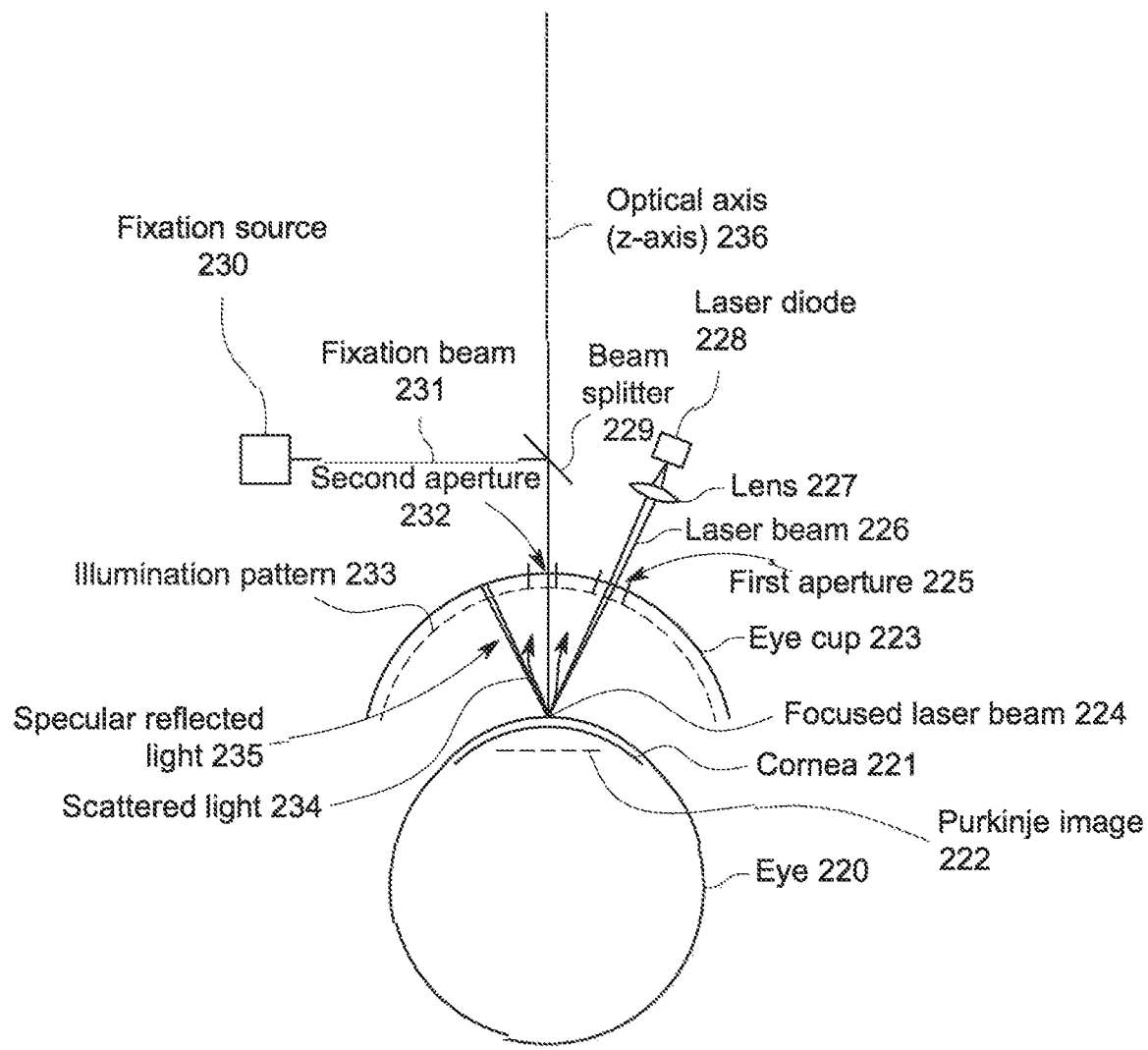
FIG. 2C illustrates a top view of a diagram of an auto-capture system according to some embodiments.
Figure 3:
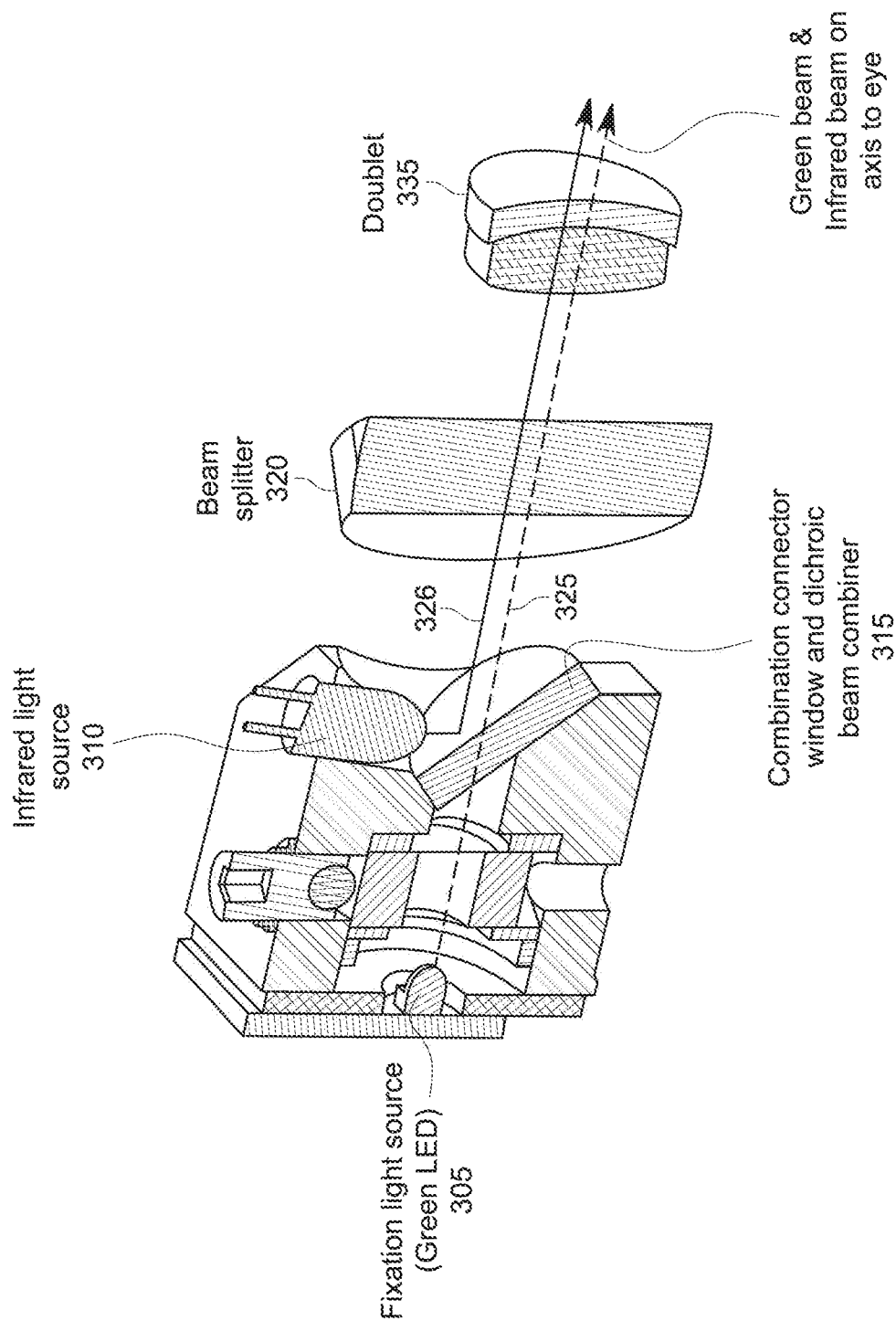
FIG. 3 illustrates a corneal topography system that includes IR illumination (e.g., an IR beam) and a green fixation beam being aligned on-axis into a patient's eye to detect pupil edges according to some embodiments.

FIG. 2C shows alignment of the eye with a ranging beam such as a laser beam focused on the cornea, in accordance with some embodiments. In some embodiments, an eyecup 223 comprises a first aperture 225 to pass the ranging laser beam and a second aperture 232 to pass the scattered light 234 from ranging laser beam. The laser beam 226 may comprise a laser beam from any suitable laser source such as a laser diode 228. Light from the laser source may be passed through a lens 227 to focus the laser beam to a waist near the cornea 221. In some embodiments, the laser beam is inclined relative to the optical axis of the system at any suitable angle, such as an angle from about 20 degrees to about 60 degrees, such that the laser beam spot moves across the cornea 221 as the topography system moves relative to the eye along the optical axis (Z-axis) 236, as described herein. Prior to measuring the eye, the laser beam angle may be adjusted to cross the optical axis where the vertex of the cornea is to be positioned when aligned with the topography system along the optical axis. The laser beam 226 may also be focused where it crosses the optical axis 236, so as to decrease the spot size and improve positioning accuracy. In some embodiments, when the vertex of the cornea is positioned along the optical axis at the intended position along the optical axis, the focused waist of the laser beam 226 may appear as a spot of light in the camera image so as to overlap with the image of the reflection from the fixation light as described herein. In some embodiments, the focus of the laser beam at the location where the beam crosses the optical axis may be sufficiently small to allow accurate alignment of the eye along the optical axis and can be focused to any suitable size, for example within a range from about 10 microns to about 100 microns, Although reference is made to a beam waist, the focused spot need not comprise a diffraction limited spot, and the beam waist may correspond to an image of the output aperture of the laser diode 228, for example. In some embodiments, the light from the focused laser beam is back scattered from the cornea generally along the optical axis towards the second aperture 232 and the imaging optics of the corneal topography system. In some embodiments, the topography images may comprise the scattered light 234 from focused laser beam 226 illuminating the cornea. In some embodiments, the laser beam light reflected from the cornea 221 with specular reflection 235 (i.e. mirror like reflection) may be reflected from the tear film on the anterior surface of the cornea 221 at an angle to the optical axis similar to the angle of the laser beam toward the cornea but in an opposite direction. This specular reflected laser beam light 235 may be blocked by the eyecup 223 or other suitable structure. This reflection of the specular light away from the second aperture 232 can improve the contrast of the image of the scattered light from the cornea. In some embodiments, the eyecup 223 comprises the first aperture 225 to pass the laser beam. The second aperture 232 is sized to pass the fixation beam, the pattern of reflected light from the cornea in order to image the pattern with the camera, the scattered light 234, and the fixation beam reflected from the cornea. The illumination pattern 233 is passed through the second aperture 232 so as to form the Purkinje image 222 comprising light from the illumination pattern 233 and the fixation beam 231 as described herein.

In some embodiments, the Purkinje image of the illumination pattern is located farther from the cornea than the Purkinje image of the reflected fixation beam. In some embodiments, the location of the Purkinje image varies with the distance of the object reflected from the cornea. For objects that are located closer to the cornea and reflected from the eye, the Purkinje image is located farther from the cornea. For objects that are farther from the eye, the Purkinje image is located closer to the cornea. The fixation beam may comprise a substantially collimated beam of light that corresponds to an object far from the eye, e.g. approximating infinity. The illumination pattern reflected from the eye corresponds to a distance from the cornea that is closer to the cornea than the reflected fixation beam, and the Purkinje image of the illumination pattern is located farther from the cornea than the Purkinje image of the reflected fixation beam.

The components, structures and features shown with reference to FIG. 2C can be combined with embodiments of the topography system as described herein. For example, in some embodiments, a fixation beam 231 may pass through the second aperture 232 that receives the scattered light 234 from the cornea. In some embodiments, the eyecup 223 may comprise any suitable illumination pattern such as Placido disks, point sources of light, point sources of light arranged along circles to approximate a Placido disk, or a grid pattern, for example. In some embodiments, the illumination pattern 233 is configured to reflect from the cornea form a Purkinje image 222 (virtual image), such as the first Purkinje image 222 at a location below the cornea. The fixation light beam 231 may comprise approximately collimated light that reflects from the cornea to form a portion of Purkinje image 222 that forms near the center of the Purkinje image of the illumination pattern as described herein. In some embodiments, the scattered laser light 234 from the cornea 221 overlaps with the Purkinje image of the fixation beam 231 near the center of the illumination pattern as described herein.

Figure 2D:
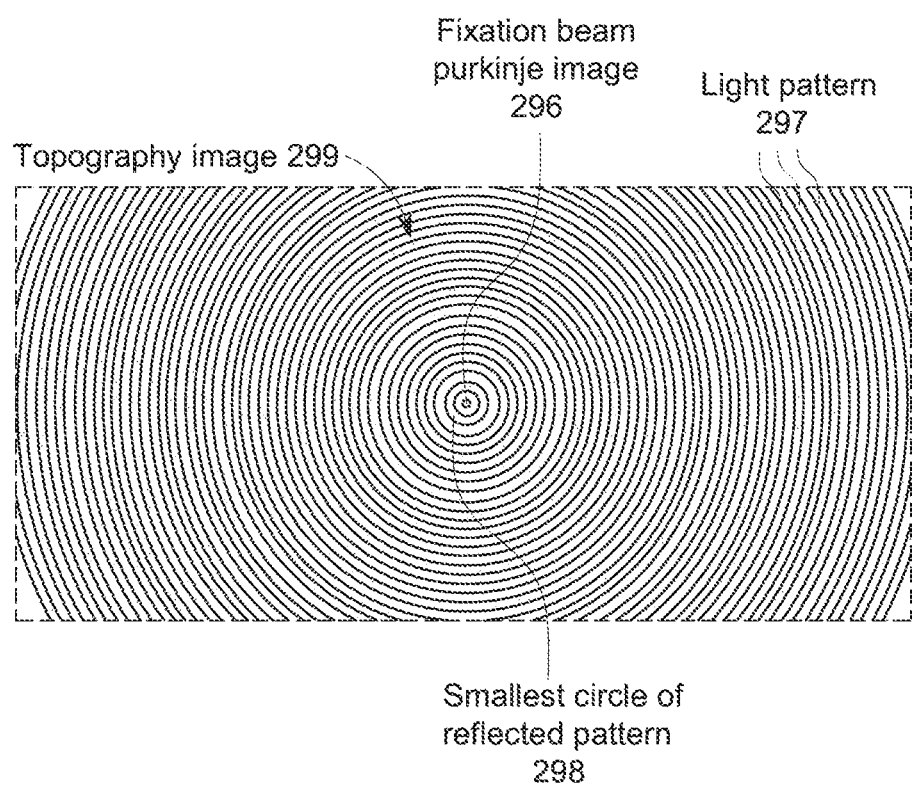
FIG. 2D illustrates a topography image of a ring pattern according to some embodiments.

FIG. 2D illustrates a topography image 299 produced by the mobile communications device-based corneal topography system. In some embodiments, a light pattern 297 comprises rings of concentric circles of varying diameters. The size, shape and location of the light pattern is related to the shape of the cornea and can be used to derive corneal topography data. For example, with steeper corneas the light pattern is smaller in the camera image and with flatter corneas the light pattern is larger. With astigmatic corneas, the light pattern can be distorted, being larger in one direction and smaller in another direction.

In some embodiments, the fixation beam Purkinje Image 296 is smaller and inside of the smallest boundary of the pattern, such as a circle 298.

The light pattern reflected from the cornea can be shaped and processed in many ways. In some embodiments, the light pattern comprises a plurality of continuous rings of light, such as a rings of a Placido disk. Each of the continuous rings can be processed with image processing to determine a plurality of discrete points corresponding to a plurality of locations of each ring. Alternatively, the light pattern may comprise a plurality of discrete light sources located along circles corresponding to rings of a Placido disk, and the locations of each of these light sources determined. The light pattern locations may be derived from the rings or the discrete sources of the light pattern in order to generate the corneal topography data. The light pattern locations may corresponds to a plurality of concentric circles with deceasing diameters. In some embodiments, a plurality of LED light elements may form and/or generate the light pattern.

In some embodiments, the image of the fixation beam may overlap with the alignment beam which may include the second wavelength of light from the alignment beam scattered from the cornea and the first wavelength of light from the fixation beam reflected from the cornea. In some embodiments, a distance across the alignment beam on the cornea may be within a range of 5 microns to 200 microns, optionally within a range of 10 microns to 150 microns, or optionally within a range of 20 microns to 100 microns. In some embodiments, a distance across the fixation beam in a Purkinje image of the eye may be within a range of 10 microns to 300 microns, optionally within a range of 25 microns to 200 microns, or optionally within a range of 50 to 150 microns.

In some embodiments, a reticle may be displayed on the mobile communication device screen to facilitate alignment, for example when the alignment beam overlaps the fixation beam. While the beams can be sized in many ways, the overlapping area of the beams in the image may correspond to a distance across the cornea within a range of 10 microns to 200 microns, optionally a range of 15 microns to 125 microns, or optionally a range of 20 microns to 75 microns.

In some embodiments, the illumination system may include a Placido ring assembly comprising a plurality of rings, wherein an innermost concentric ring of the camera image has a larger diameter than a distance across the fixation beam, or a distance across the ranging beam. In some embodiments, the illumination system may include a Placido ring assembly including a plurality of concentric rings, wherein the plurality of concentric rings is formed by a plurality of light-emitting diodes (LEDs) at discrete separated locations along a plurality of circles. In some embodiments, the illumination system may include a Placido ring assembly including a plurality of concentric rings, wherein the plurality of concentric rings is formed by a geometry of a Placido ring component, and the Placido ring component may be illuminated by a plurality of light-emitting diodes (LEDs). In some embodiments, in the corneal topography system, the luminescence intensity of pattern from the illumination system at the cornea may be within a range from 10 lux to 500 lux, optionally from 25 lux to 250 lux and optionally from 50 lux to 125 lux In some embodiments, the illumination system may comprise or include a Placido ring assembly comprising a plurality of concentric rings, the plurality of concentric rings emitting a third wavelength of light, the third wavelength of light different from the first wavelength of light, e.g. of the fixation beam, and the second wavelength of light, e.g. of the ranging beam. In some embodiments, when a patient is being examined on the mobile communication device-based corneal topography system, the eye of a patient looks downward from horizontal at an angle within a range of 2.5 degrees to 15 degrees towards the fixation target beam, or optionally looks downward a range of 5 degrees to 10 degrees towards a fixation target beam. In some embodiments, the alignment beam may be inclined relative to an optical axis and focused to a cross-sectional size on the cornea to position the vertex of the cornea along the optical axis with an error of no more than 150 microns when the fixation beam overlaps with the alignment beam in the image, and optionally wherein the error is no more than 100 microns, optionally no more than 50 microns and optionally no more than 25 microns. In some embodiments, when a patient is being examined on the mobile communication device-based corneal topography system, the eye of a patient looks at a fixation target beam along a horizontal axis. In some embodiments, when a patient is being examined on the mobile communication device-based corneal topography system, the eye of a patient looks down at an angle from horizontal within a range of 0.1 to 2.5 degrees towards the fixation beam.

Referring again to FIG. 2B, the mobile communications device-based corneal topography system may comprise one or more ergonomic configurations, according to some embodiments. In some embodiments, the patient looks downward at an angle 890 relative to horizontal toward the fixation target embodiments, an additional design consideration may be that an image of a subject's cornea on the mobile communication device's display (e.g., the reflected image) be positioned at a downward angle with the horizontal line connecting an examiner and an examination subject (or patient). A term of art used by movie directors and cinematographers that pertains to this may be referred to as "eye line". That is an imaginary line connecting the eyes of two actors in a scene. In a corneal topography system, an "eye-line" between an examiner and a subject has traditionally been in a horizontal plane. The "eye-line" refers to a condition where the eye of the examiner should be aligned near a horizontal plane with the eye of the subject being examined. FIG. 2B illustrates a horizontal eye line 256 between an examiner and an examination subject. The line between the examiner's eye 282 and the image of the cornea on the mobile communication device display is in a downward direction. In other words, the examiner is looking downward to the corneal image as is illustrated by the line identified as angle 899 relative to horizontal. In embodiments of a mobile communication device-based corneal topography system, it may be preferable to have a corneal topography image on the mobile communication display be reasonably aligned both horizontally and vertically such that the eye-line passes through a center of a live camera image of mobile communication device display. In some embodiments, the examiner may look along a horizontal axis towards the image on the mobile communication device display. In some embodiments, the examiner may look down at an angle from horizontal within the range of 0.1 to 2.5 degrees towards the display of the mobile communication device.

This allows ease-of-use for an examiner in that it may maintains the same or similar horizontal plane eye-line relationship that existed when the Examiner utilized the slit-lamp microscope. In other words, the examiner is used to such a horizontal plane eye-line positioning when the examiner operates the slit-lamp microscope. In some embodiments, the mobile communication device-based corneal topography system, which is attached to the slit-lamp microscope, does not change this horizontal plane eye-line relationship. In some embodiments, Aa mobile computing device-based corneal topography system may comprise a bulkhead and a slit lamp mounting plate and/or mounting assembly according to embodiments. In some embodiments, a bulkhead or positioning plate may be utilized to align and/or attach other pieces of a smartphone-based corneal topography system in place in order to enable efficient operation. In some embodiments, a bulkhead or a positioning plate may include a recess for a Placido illumination system 267 and/or eye piece 258. In some embodiments, a mounting assembly (e.g., a positioning plate may attach to an optical bench or corneal topography optical housing) may be utilized to connect to a slit lamp microscope mounting assembly. In embodiments, a mobile communication device-based corneal topography system may be attached (or piggy-backed) onto a slit-lamp microscope in order to maintain examination accuracy.

In some embodiments, a mobile communication device-based corneal topography system may also utilize infrared (IR) illumination (or a similar wavelength illumination to enable or initiate pupil edge detection. In some embodiments, the IR beam is transmitted through the pupil and reflected from the retina, such that the pupil of the eye appears lighter than the iris. This retro-illumination of the pupil can facilitate detection of the edge of the pupil. FIG. 3 illustrates a corneal topography system or housing that includes IR illumination (e.g., an IR beam) and a green fixation beam being aligned on-axis into a patient's eye according to some embodiment. In some embodiments, the on-axis alignment of the infrared illumination and green fixation beam may allow for edge detection of a patient's pupil during dark conditions (e.g., without the Placido rings being illuminated) (scotopic conditions), during medium light conditions (mesopic conditions) and during light conditions—photopic conditions (e.g., with the Placido rings being illuminated). In other words, the corneal topography software application may generate pupil edge measurements in light and/or dark conditions. In some embodiments, the IR light source may introduce the infrared beam coaxially, aligned with the green fixation beam and on axis with a patient's line of sight. In some embodiments, an advantage of coaxial illumination of the IR beam and the green fixation beam is that an operator and the corneal topography smartphone software may image the "red reflex" (retro-illumination) and see opacities in an optically significant part of the patient's visual system (e.g., a central ~6 mm diameter of the cornea and lens, which is an approximate measure depending on a patient's pupil size). This advantage may be in addition to the coaxial alignment of the infrared beam and green fixation beam allowing the corneal topography software application to image the pupil edge for pupil size measurement in dark and light conditions.

In FIG. 3, in some embodiments, the corneal topography system or housing may include a fixation source (e.g., green LED) 305, an infrared light source 310 (IR LED), a first lens assembly 315, a second lens assembly 320, and/or a doublet 335. In some embodiments, the green fixation source 305 may a green LED that transmits a green fixation beam 325. In some embodiments, the green fixation beam 325 may be transmitted on axis to a patient's eye, as is illustrated in FIG. 3. In some embodiments, the green fixation beam 325 may be transmitted through a first lens 315, which may be a tilted lens. In some embodiments, the first lens 315 may be tilted which may introduce an astigmatism in the green fixation beam. In some embodiments, the green fixation beam 325 may then pass through a second lens 320, which may be a tilted lens. In some embodiments, the second tilted lens may correct for the astigmatism introduced by the first lens 315. In some embodiments, the green fixation beam 325 may pass through a doublet 335 on its way to the patient's cornea. In some embodiments, an infrared light beam 326 may be introduced in front of the first lens 315 and reflects off of the front surface of the first lens 315. In some embodiments, the infrared light beam 340 may pass through or be transmitted through the second lens 320 and/or the doublet 335 to the patient's cornea. In some embodiments, the infrared light source 310 may cast diffuse infrared light onto the patient's pupil in order to the illuminate the patient's pupil at an infrared spectrum. Because, the infrared light beam 326 may be diffused, the system may not have to correct for an astigmatism. In some embodiments, the infrared light source may be an LED having a wavelength of 780 nm (+/−15 nm). In some embodiments, the infrared light source may be a Thorlabs LED780E. In some embodiments, the light source may generate a light beam substantially close to infrared light spectrum as long as the light source illuminates the subject's eye.

In some embodiments, in order to perform pupil edge detection, the fixation light source (e.g., green LED) 305 and the infrared light source 310 may be activated and/or turned on. In some embodiments, the green fixation light source 305 and the infrared light source 310 may be activated by an operator turning on switches or controls of the corneal topography system or housing. In some embodiments, computer-readable instructions executable by one or more processors on a topography outboard or PCB of a corneal topography system or housing may cause signals to be transmitted to the fixation light source 305 and the infrared light source 310 in order to turn on the fixation light source 305 and/or the infrared light source 310. In some embodiments, computer-readable instructions executable by one or more processors on the mobile communication device may cause signals, commands and/or instructions to be transmitted to the corneal topography system or housing to activate or turn on the fixation light source 305 and the infrared light source 310. Although FIG. 3 illustrates a first lens, a second lens and a doublet, other optical components may be utilized by the corneal topography system in order to direct the green fixation beam and/or the IR beam to the patient's cornea. Although FIG. 3 and the discussion above identifies an IR beam and a green fixation beam, other wavelengths and/or colors may be utilized in place of or in addition to the IR beams and green fixation beams as long as these other light beams are detectable in light and/or dark conditions and illuminate the eye.

Figure 3A:
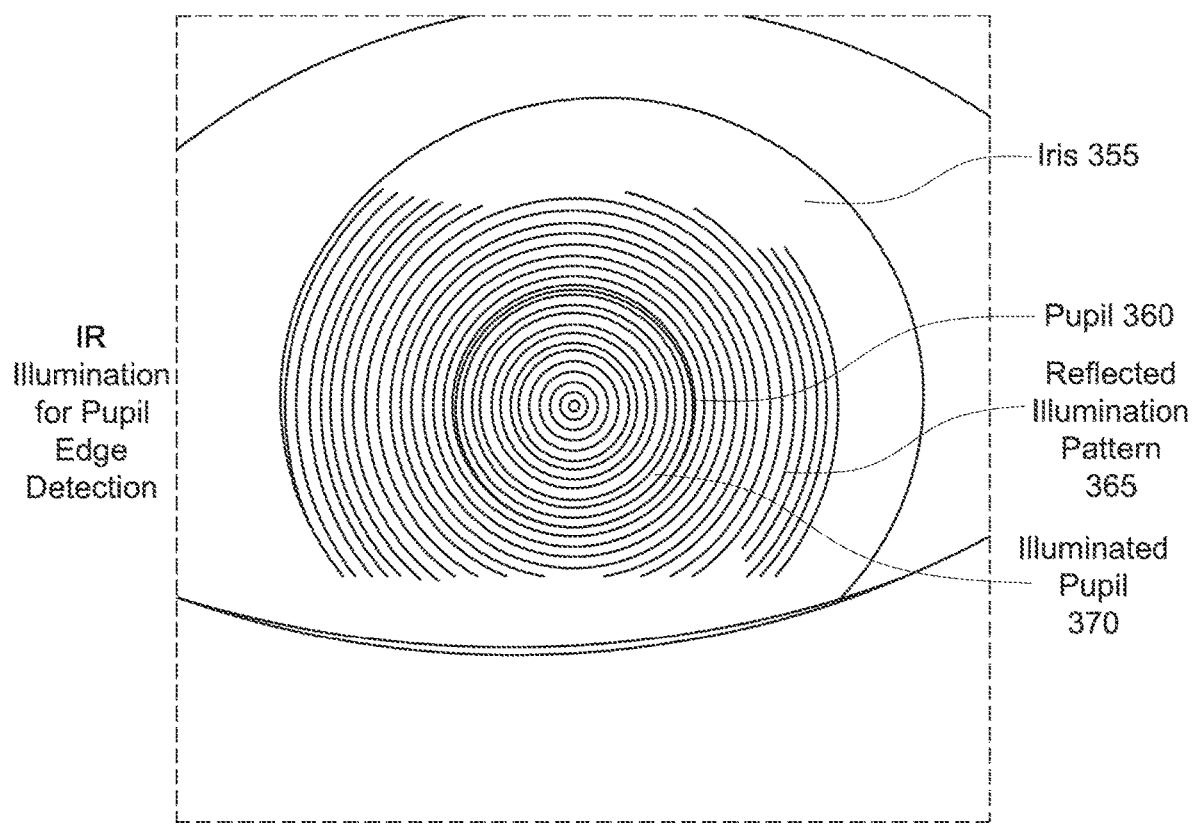
FIG. 3A illustrate an image resulting from use retro illumination of the pupil for pupil edge detection according to some embodiments.

FIG. 3A illustrate results of utilization of the IR illumination system for pupil edge detection according to some embodiments. As is illustrated in FIG. 3A, the patient's pupil 360 may be illuminated by infrared illumination, which is reflected from the retina, such that the pupil appears lighter than the iris. In FIG. 3A, the eye may be in a dark or non-illuminated setting or environment. In some implementations, the eye may include an iris 355, a pupil 360, a reflected illumination pattern 365 (e.g., a reflected Placido ring pattern), and a pupil illuminated by an infrared light source as described herein. Work in relation to the present disclosure suggests that retro-illumination of the pupil is well suited for combination with smart phone cameras as described herein, because the retro illumination of the pupil provides a sufficiently bright pupil for the edge of the pupil to be readily visible in the camera image, and the smart phone camera may comprise sufficient sensitivity to wavelengths that are barely perceptible or substantially imperceptible by the human eye to make the pupil readily visible in the camera image, such as wavelengths from about 750 to 850 nm.

Although reference is made to edge detection with retro-illumination of the pupil, an IR light source can be used to illuminate the iris and detect the pupil without retroreflection. For example, IR light sources to transmit light obliquely toward the cornea so as to illuminate the iris and detect the boundary between the iris and the pupil.

In some embodiments, the iPhone 7-Plus is a high-end mobile communication device that includes a high-end camera, a high-end lens and image processing hardware and/or software. Even with a high-level mobile communication device platform, (such as the Apple iPhone 7 and other similar Android-based smartphones made by Motorola and Samsung), the mobile communication device may have tiny variations in lens position relative to the mobile communication device camera sensor. For example, this is true with the Apple iPhone7. In addition, the high-level mobile communication device platforms also have very tiny variations in adjustment needed to set (or lock) focus and/or zoom optimally for the corneal topography system Keplerian telescope system resident or installed in the corneal topography system or housing. Accordingly, individual measurements or settings may need to be made for each individual mobile communication device (e.g. iPhone) camera-and-lens subsystem. Then, individual .ini files (e.g., configuration files) may need to be created for each individual mobile communication device to incorporate those unique settings. Such a setup and/or requirement is not useful in a production or manufacturing environment because time and/or resources would be necessary to measure the variations in the cameras and/or lens of the mobile communication device and then to record or store the identified settings for utilization later in configuring the corneal topography system.

In a new and novel embodiment, as illustrated in FIG. 4A, a new configuration of a mobile communication device-based corneal topography system includes moving an image sensor, one or more processors, one or more memory devices and/or image processing hardware and software into the corneal topography system or housing. In some embodiments, the image sensor (or camera sensor), one or more processors, one or more memory devices and image processing hardware and/or software may be installed on one or more printed circuit boards (PCBs) or an outboard, and the PCBs or outboard may be installed in a corneal topography system or housing. The specification herein refers to a topography-specific PCB or a topography-specific outboard, but this apparatus may also be referred to as a topography outboard, a topography-specific chipset, or a topography-specific system on a chip (SoC). In some embodiments, the topography-specific PCB or outboard may be a single printed circuit board and/or maybe two or more PCBs coupled or connected to each other. In addition, the topography-specific PCB or outboard may also have components or assemblies that perform other functions including having a communications interface (e.g., such as a USB or Ethernet communication interface). In some embodiments, while the specification refers to a corneal topography system or housing, the image sensor, one or more processors, one or more memory devices, the image processing hardware or software, and/or other components or assemblies may be i) installed, located or positioned within a single physical housing or multiple physical housings or ii) have some of the image sensor, one or more processors, one or more memory devices, the image processing hardware or software, and/or components or assemblies mounted, attached, coupled or connected to one or more physical housings. In other words, the description herein is not limited to all of the above listed devices, components or assemblies being located within one physical corneal topography housing. For example, in some embodiments, some of the devices, components or assemblies may be partially contained within the corneal topography housing and others may be completely contained within the corneal topography housing. For example, in some embodiments, some of the devices, components or assemblies may be partially contained within one or more corneal topography housings while others are attached to, coupled to or connected to other devices, components and/or assemblies that are not within corneal topography housings.

In some embodiments, the image sensor (or camera sensor) and other components (e.g., processors, image processors, memory devices, computer-readable instructions, etc.) may be mounted on a circuit board. In some embodiments, a circuit board may be mounted to a rear surface of corneal topography system or housing, although the location of the circuit board may not be limited a rear surface. In some embodiments, the image sensor (or camera sensor) may be installed in a position that is a horizontal center of the rear surface of the corneal topography system or housing and may also be directly be aligned with a rest of the slit-lamp microscope which is aligned with the corneal topography system. In some embodiments, the image sensor (or camera sensor) may be installed in other positions and on other surfaces besides a horizontal center of a rear surface. Accordingly, the specification does not limit the location of the image sensor (or camera sensor) within the corneal topography system or housing as the location of the image sensor may be within any location of the corneal topography system or housing.

FIG. 5, which will be described later, may utilize the mobile communication device camera rather than the image sensor (or camera sensor) of the corneal topography system of FIG. 4A. However, in FIG. 5, because the mobile communication device may be designed, customized and/or fabricated for the corneal topography system, any variations in the lens position and/or the adjustments for focus and/or zoom may be eliminated because the mobile communication device camera sensor will be affixed at the exact focal plane of the Keplerian telescope system of the corneal topography system, eliminating the standard lens typically installed in front of the camera sensor in most modern mobile communication device. Additionally, the mobile communication device may be be manufactured according to custom specifications provided by the maker or developer of the mobile communication device-based corneal topography system.

FIG. 4A illustrates a block diagram of a corneal topography system including system components (including an image sensor or camera sensor) for corneal topography at least partially contained within a housing according to according to some embodiments. In some embodiments, as illustrated in FIG. 4A, the corneal topography system 407 may be connected, coupled or attached to a custom-designed and fabricated mobile communication device 470. In some embodiments, the corneal topography system 407 may be positioned adjacent to a surface of the mobile communication device 470 and may be connected via a ribbon cable (e.g., a USB-3 ribbon cable). In some embodiments, the corneal topography system or housing 407 may be connected or coupled to a slit lamp microscope mount 475 to allow adjustment of the corneal topography system or housing with respect to the patient's eye. In some embodiments, as illustrated in FIG. 4A, the corneal topography system or housing 407 may comprise a power supply 411, an image path 412, a communications interface or communications processor 425, a topography-specific PCB or outboard 412, a Placido ring illumination control system 450, a fixation light source 452, an infrared light source 453 and/or a ranging beam light source 451. In some embodiments, the corneal topography system or housing 407 may further comprise an illumination system 457 (e.g., a Placido rings illumination system) and/or a rest 458. In some embodiments, a patient's head may rest on a chin rest of the slit lamp microscope with a curved plastic strap to position the forehead against the corneal topography system. In some embodiments, fixating the chin and forehead may allow for stabilization of the head relative to the microscope (and thus the corneal topography system.) In some embodiments, the illumination system 457 (e.g., Placido ring illumination system) may include one or more lights (e.g., LEDs) to illuminate a specific pattern that may be reflected off of a patient's cornea. In some embodiments, the custom-designed or fabricated mobile communication device 470 may comprise one or more processors, one or more memory devices, operating system software, application software, a display and/or a communication interface 425. In addition, although not shown in FIG. 4A, the mobile communication device 470 may also include GPS transceivers, cellular transceivers (3G, 4G, or 5G), wireless local area network (Wi-Fi) transceivers, NFC transceivers, and/or other components and/or software. In some embodiments, as illustrated in FIG. 4A, the topography-specific PCB/outboard or control circuitry 412 may comprise an image processor 440, one or more processors 415, one or more memory devices 416, computer-readable instructions stored in the one or more memory devices 417 and/or firmware 418. In some embodiments, the topography-specific PCB or outboard 412 may comprise communication circuitry and/or a communication interface 425. The topography-specific PCB or outboard 412 may not be required to utilize or include all the components or assemblies illustrated in FIG. 4A. For example, in some embodiments the one or more processors 415 may include image processing capability (and so a separate image processor may not be needed). In some embodiments, for example, the one or more memory devices 417 may include all the driver and/or application software and firmware 418 may not be needed in certain embodiments of topography-specific PCB or outboard.

In this new and novel corneal topography system or housing, an imaging subassembly (which includes Keplerian telescope lenses and/or beam folding mirrors) may reflect a Placido rings image on a patient's cornea and the image sensor (or camera sensor) 410 may capture a reflected Placido rings image (or an image of another illuminated pattern). In some embodiments, because the image sensor (or camera sensor) 410 may be placed at a specific position and because the imaging subassembly and resulting imaging path 430 may have specific dimensions, the reflected Placido rings image (or image of another illuminated pattern) may be received at the image sensor or camera sensor 410 at a corneal image plane at a desired vertex distance from the patient's eye (or cornea). In some embodiments, the Placido rings image (or image of another illuminated pattern) may be reflected or projected into the camera sensor without using any type of zooming functionality. In some embodiments, the image sensor, camera sensor or detector may be a CMOS-sensor or may be a CCD sensor (such as a Sony IMX250 CMOS sensor).

In some embodiments, a Keplerian telescope of the corneal topography system may project a Placido rings image directly into the image sensor or camera sensor without interposing a standard camera lens on an outer housing of a mobile communication device in front of the camera sensor. In some embodiments, the zoom may be set and defined by the optical components of the Keplerian telescope system. In some embodiments, the zoom may not able to be tweaked or altered by any adjustment of the mobile communication device camera optical zoom settings because there is no camera lens affixed in front of the image sensor of the corneal topography system. In some embodiments, software-controller digital zoom is still possible. In addition, in some embodiments, eliminating the mobile communication device camera lens and utilizing the Keplerian telescope system (which is in the corneal topography system) along with the image sensor or camera sensor 410 of the corneal topography system or housing also eliminates mobile communication device camera lens positioning errors. In some embodiments, this leads to design where the focus of the corneal topography system may be locked during the manufacturing without having to tweak or adjust each unit in a post-manufacture calibration.

In some embodiments, the projected Placido rings image (or other illuminated pattern image) may be projected or reflected to the image sensor or camera sensor 410 at a perfect focus. This configuration eliminates the need to use the mobile communication device camera and/or lens (and the resulting variations therein) to capture the reflected Placido rings image (or other illumination pattern image). In addition, because the corneal topography system or housing may comprise the image or camera sensor, the image processing hardware and/or software and/or other corneal topography software may be moved into the corneal topography system or housing 407. In some embodiments, the image processing hardware and/or software and/or other corneal topography software may be located on the topography-specific outboard or housing.

In some embodiments, the topography-specific PCB or outboard 412 may further comprise computer-readable instructions stored on the one or more memory devices that were described above (e.g., non-volatile memory devices 416 and/or firmware 418). In some embodiments, the computer-readable instructions may be accessed and executed by one or more processors 415 or 440 in order to control operation of other components in the corneal topography system or housing 407. In some embodiments, the computer-readable instructions may be executed by one or more processors or controllers 415 or 440 to control operation (e.g., activation or deactivation) of 1) a Placido rings illumination subsystem (or other illumination pattern subsystem); 2) fixation LED assembly (e.g. a Green LED assembly) and generated fixation beam; 3) a LED ranging laser assembly (e.g., a Red LED assembly) and generated ranging beam and/or 4) an infrared LED assembly and generated infrared light beam. In some embodiments, the Bluetooth communication transceiver (or PAN communication transceiver) from the previously disclosed corneal topography system may be eliminated because the topography-specific PCB or outboard 412 may either communicate with the other components via wired connections (and/or wired communication protocols). In some embodiments, the components may be mounted or installed on the topography-specific PCB or outboard 412 and thus may be communicated with over a wired communications interface or communication circuitry on the topography-specific PCB or outboard 412.

In some embodiments, the corneal topography software may be stored in the one or more memory devices 416 and 418 on the topography-specific PCB or outboard 412. In some embodiments, for example, topography library software (e.g., computer-readable instructions) may be stored in firmware 418 that may be executable by the one or more processors 415 or 440 that are installed on the topography-specific PCB (or outboard) or in other memory devices in the corneal topography housing. In some embodiments, the one or more processors may include an image processor that is specifically designed to handle imaging processing functions and/or analysis. In some embodiments, firmware 418 on the topography-specific PCB (or outboard) 412 may store certain portions of the corneal topography software may include instructions that are executable by one or more processors or an image processor 440 to handle data intensive functionality (such as executing and initiating the corneal topography system auto-capture functionality, the Placido rings image capture, the Placido rings edge detection and/or the corneal topography power mapping), while allowing the one or more other processors 415 to initiate and execute other functionality such as activation of other components and/or transfer of information between the corneal topography system or housing 407 and the custom-designed and fabricated mobile communication device 470. In some embodiments, the one or more processors and/or related application software in the corneal topography system or housing 407 may then only communicate or transfer the corneal topography related images and datafiles to the custom-designed and fabricated mobile communication device for display on the mobile communication device display. In some embodiments, the custom-designed and fabricated mobile communication device may then upload the necessary corneal topography images to a cloud-based server, without having to perform any image processing at the mobile communication device.

In this new configuration or embodiment (as illustrated in FIG. 4A), the "intelligence" of the mobile communication device-based corneal topography system may be moved into a physical housing (or one or more physical housings) that is outside of the custom-designed or fabricated mobile communication device. Accordingly, a high-end mobile communication device with significantly processing power and/or an image processing chipset is no longer needed to perform the corneal topography software functionality. In some embodiments, a custom-designed and manufactured mobile communication device may be utilized as the mobile communication device in the mobile communication device-based corneal topography system. In some embodiments, an operating system may be created and developed for the custom-designed and fabricated mobile communication device by the developer and creator of the corneal topography system or housing (e.g., the corneal topography system), which is Intelligent Diagnostics, LLC. In some embodiments, the custom-designed and fabricated mobile communication device 470 may only be required to have a monitor or display, a custom-designed and/or developed (and thus proprietary and closed) operating system, one or processors, a wired communication interface or communication circuitry (e.g., USB or Ethernet communication circuitry), and/or a wireless communication transceiver (e.g., a WiFi transceiver); a personal area network transceiver—Bluetooth; and/or a cellular (3G, 4G, or 5G) transceiver, although many other components and/or software applications may also be resident within the mobile communication device.

Figure 4B:
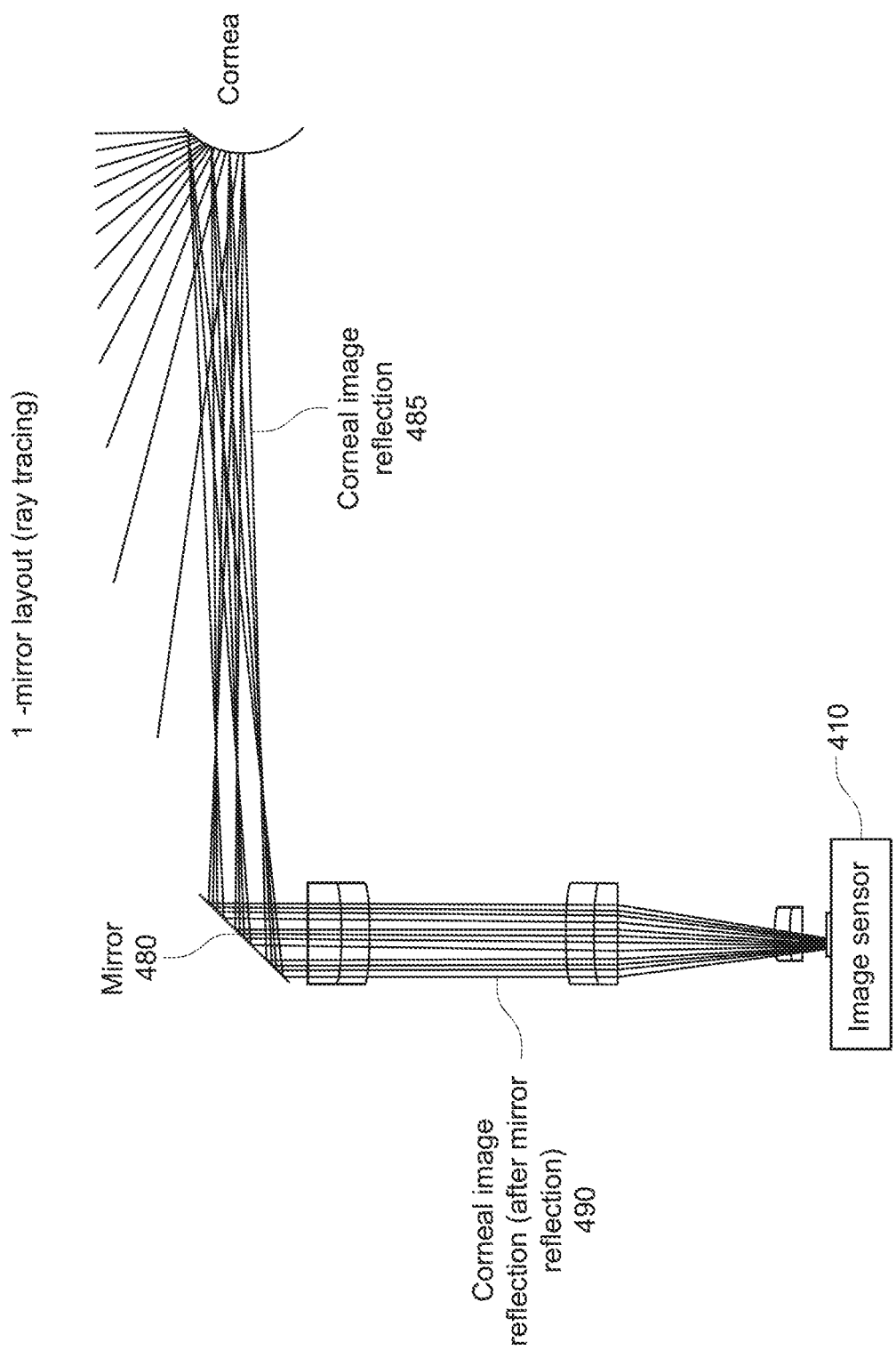
FIG. 4B illustrates a ray drawing of a corneal topography system including a single mirror design according to some embodiments.
Figure 4C:
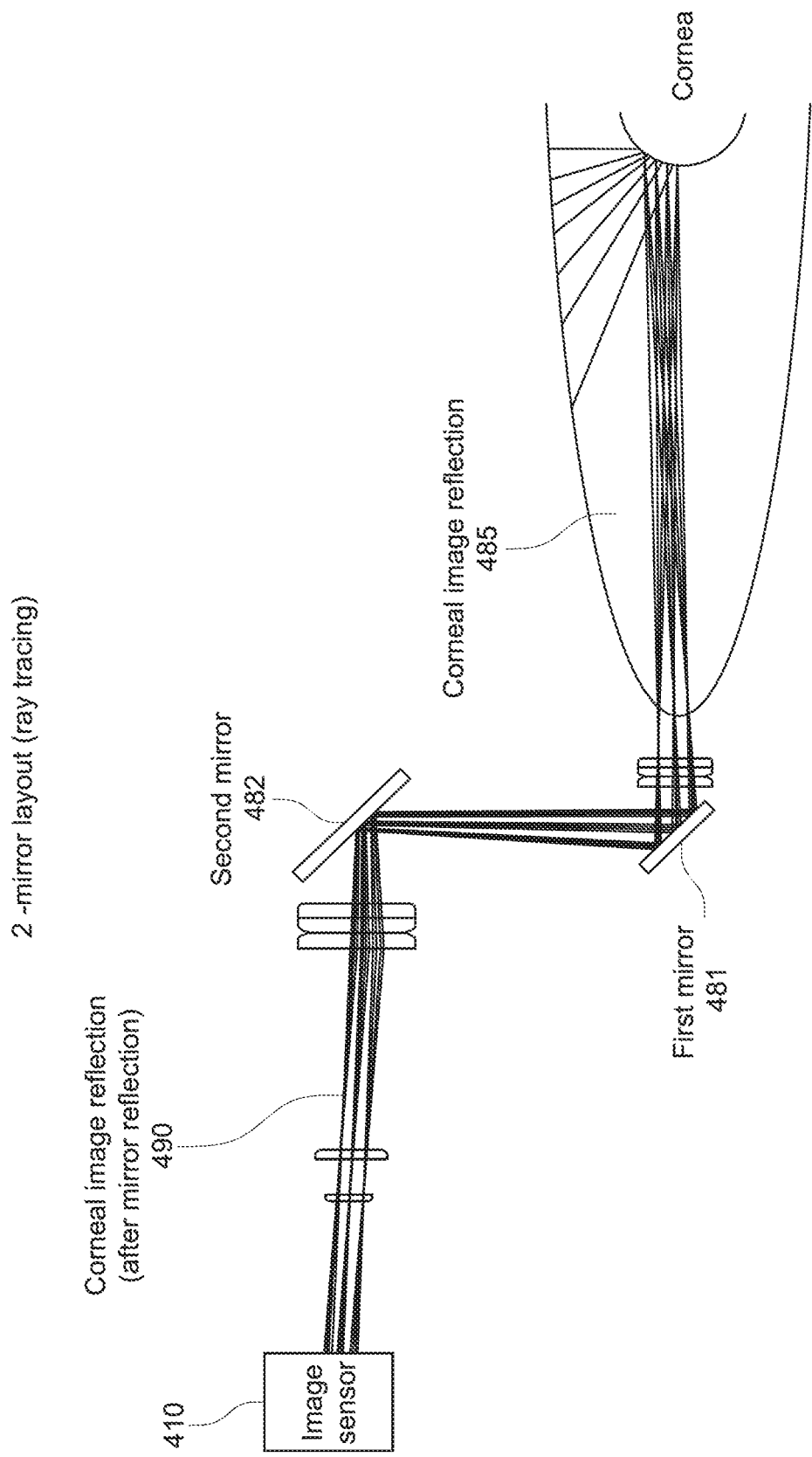
FIG. 4C illustrates use of two mirrors for folding an image beam path in a corneal topography system according to some embodiments.

With this new system configuration, the corneal topography system may still utilize one or more mirrors to fold an image beam path created by the Keplerian telescope optical subassembly. However, it is not necessary to utilize the mobile communication device camera that was discussed in the prior ID patent applications. Thus, in the embodiment illustrated in FIG. 4A, the reflected image beam path may be decoupled from the mobile communication device camera and/or the entrance pupil location of the associated lens. As discussed above, in FIG. 4A, the image sensor or camera sensor 410 may integral and/or integrated into the corneal topography system or housing 407 (and specifically may be integrated as part of the topography-specific PCB or outboard 412). In some embodiments of this new corneal topography system, the telescope optical system beam path may be short enough so that one mirror or two mirrors may be utilized for folding an image beam path. FIG. 4B illustrates use of one mirror for folding an image beam path in a corneal topography system according to some embodiments. FIG. 4C illustrates use of two mirrors for folding an image beam path in a corneal topography system according to some embodiments. In some embodiments, as illustrated in FIG. 4B, a reflected illuminated pattern image (e.g., a reflected Placido rings image) may be transmitted or reflected to an image sensor 410 in the corneal topography system or housing after being reflected by a mirror 480. In some embodiments, as illustrated in FIG. 4C, a reflected illuminated pattern image (e.g., a reflected Placido rings image) may be transmitted or reflected to an image sensor 410 in the corneal topography system or housing after being reflected by a first mirror 481 and/or a second mirror 482. In some embodiments, no mirrors may be necessary for folding an image beam path. Thus, in the last embodiment, mirrors utilized for folding an image beam path may be eliminated from the corneal topography optical system. In some embodiments, mirrors and/or lenses may still be utilized to introduce or direct the fixation beam and/or infrared (IR) light to the patient's eye or cornea or for other features or functionality of the corneal topography system.

In this new system configuration (FIG. 4A), the topography-specific PCB or outboard 412 may be placed in different locations relative to the corneal topography system or housing 407 and the mobile communication device to which this subsystem is attached. In some embodiments, the position of the topography-specific outboard or PCB 412 may 'float' or be moved relative to a position of the custom-designed and fabricated mobile communication device 470. In some embodiments, the position of the topography-specific PCB 412 or outboard may be moved as long as the image sensor or camera sensor 410 may be aligned to receive the reflected Placido rings image (or other illumination pattern image). Thus, in some embodiments, the position of the Placido rings assembly (or other pattern illumination assembly) may be exactly in a horizontal midline of the custom-designed and fabricated mobile communication device, even if the typical mobile communication device camera is off to one side or near to the top edge of the mobile communication device (e.g., as in the iPhone 7, 8 and 10-series phones among other Android-based phones). This is because in the embodiment illustrated in FIG. 4A, the mobile communication device camera may not be utilized for image capture of the reflected Placido rings image (or other illumination pattern image). Thus, in some embodiments, the mobile communication device-based corneal topography system described in FIG. 4A may be a bilaterally symmetric product as opposed to the slightly asymmetric design that was disclosed in the previously submitted patent applications.

In addition, the movement of the corneal topography application software to memory devices in the corneal topography system or housing 407 (and specifically the topography-specific PCB or outboard 412) may provide a number of advantages. One advantage is that the developer of the corneal topography system or housing does not have to worry about mobile communication device camera drivers changing (and/or related mobile communication device operating system software changing). In other words, phone or mobile communication device manufacturers may push out updates that contain drivers and/or other tweaks which may jeopardize the operational stability of the corneal topography system. In this new configuration (FIG. 4A), the mobile communication device operating system is also custom-designed and/or developed by the corneal topography system creator or developer, so this situation should no longer be an issue. In addition, the corneal topography system developer may also have control of the operating system of the custom-designed mobile communication device (and thus updates of the OS or drivers will not be communicated to the mobile communication device unless the corneal topography system or housing developer is aware of the impact to the corneal topography system). In other words, the corneal topography system (and the software platform) may be controlled end-to-end by the developer of the corneal topography system. In some embodiments, the custom-designed and/or developed operating system may be Linux-based rather than a phone-manufacturer branded flavor of Android. In some embodiments, a version of Linux (named Yocto—which is published by Intel) may be utilized as a base operating system to run the topography-specific PCB (or outboard) 412 and other components in the corneal topography system or housing and/or the custom-designed and fabricated mobile communication device.

FIG. 4A illustrates a block diagram of a new configuration of a smartphone corneal topography system according to some embodiments. The block diagram does not represent a shape of the corneal topography system or housing and instead is drawn as a simple rectangle. In addition, the optical path labeled in the corneal topography system or housing 407 may not be indicative of the optical path (and/or components utilized therein) to transmit the reflected Placido rings image (or other illumination pattern image) to the image sensor or camera sensor 410. In addition, no lenses or mirrors are shown in the block diagram of the corneal topography system or housing although the lenses or mirrors may be present in the corneal topography system or housing 407. In other words, this Figure (FIG. 4A) is not directed to illustrating or describing the optical path in the mobile communication device-based corneal topography system. Instead, FIG. 4A is illustrating a new configuration of the corneal topography system that brings the brains and processing power into the corneal topography system or housing 407.

The mobile communication device-based corneal topography system 400 comprises a corneal topography system or housing 407, a Placido rings assembly or other pattern illumination assembly 410, a custom-designed and fabricated smartphone 470, and a slit-lamp microscope mounting assembly 475. In some embodiments, the Placido assembly (e.g., the Placido rings assembly or other pattern illumination assembly) may be mounted on one side of a corneal topography system or housing 407 and a custom-designed mobile communication device 470 may be mounted or connected to an opposite side of the corneal topography system or housing 407. In some embodiments, the corneal topography system or housing 407 may be connected or coupled to a slit lamp microscope mounting assembly 475.

In some embodiments, the corneal topography system or housing 407 may comprise an image path 430, where the image path 430 may be a path that a reflected Placido rings image (or other illuminated pattern image) travels in order to enter an image sensor or camera sensor 410. In some embodiments, the corneal topography system or housing 407 may comprise a topography-specific PCB or outboard 412. In some embodiments, the topography-specific PCB or outboard 412 may receive power from a power source 411 in the corneal topography system or housing 407. In some embodiments, the power source 411 may be a rechargeable battery. In some embodiments, the power source 411 may be connected to an external power outlet or charging pad which provides power to the power source 411. In some embodiments, computer-readable instructions 417 executable by one or more processors 415 (or firmware 418 executable by one or more processors 415) may activate an image sensor or a camera sensor 410 to capture a reflected Placido rings image (or other illumination pattern image) transmitted via the image path 430. In some embodiments, computer-readable instructions 417 stored in one or more memory devices 416 executable by one or more processors 415 (or the firmware 418 executable by one or more processors 415 or controllers) may generate instructions, commands or signals to perform operations in the corneal topography system or housing 407. For simplicity, the specification may refer to computer-readable instructions executable by one or more processors 415 from this point forward although the other embodiments described previously (e.g., firmware executable by one or more processors or controllers) may also be utilized.

In some embodiments, the computer-readable instructions 417 executable by one or more processors 415 may perform auto-capture of the reflected Placido rings image (or other illumination pattern image). In some embodiments, the computer-readable instructions 417 executable by one or more processors 415 may communicate the captured Placido rings image (or other illumination pattern image) to an image processor 440. In some embodiments, as described above, the image processor 440 may be a separate processor or device from the one or more processors 415 in order to offload intensive image processing operations from the one or more processors 415. In some embodiments, the computer-readable instructions 417 executable by one or more processors 415 may cause the image processor 440 to perform additional corneal topography functions such as Placido rings edge detection and/or the corneal topography power mapping, as well as other corneal image manipulation or processing. In some embodiments, firmware or computer-readable instructions located in an integrated circuit or a printed circuit board including the image processor 440 may be executable by the image processor 440 to perform corneal topography functions such as the Placido rings image auto-capture, Placido rings edge detection and/or corneal topography power mapping. In other words, the image processor 440 may have its own embedded software or firmware to perform corneal topography functions.

In some embodiments, the corneal topography related images and files (e.g., the reflected Placido rings image, the Placido rings edge detection, data files corresponding to the Placido rings image and/or the corneal topography power map) may be communicated to the custom-designed and/or fabricated mobile communication device 470 for display on the mobile communication device display and/or further communication or transmission to additional computing devices. The corneal topography images and/or related files may be communicated to the custom-designed and fabricated mobile communication device 470 via a communication interface or communication circuitry 425 (e.g., USB-3 interface), a cable 426 (e.g., a USB-3 Cable), and a mobile communication device communication interface or communication interface circuitry 427 (e.g., phone USB interface connector). In some embodiments, the topography-specific PCB or outboard 412 may comprise the communication circuitry or communication interface 425. In some embodiments, the communication circuitry or communication interface 425 may be a socket on the topography-specific PCB or outboard 412 and the cable 426 may be a ribbon cable. This eliminates the need for a wireless communication transceiver (e.g., a Bluetooth transceiver) in the corneal topography system or housing 407. This configuration also provides additional security for the patient data (e.g., the patient corneal topography images and related files) because the patient data may not be hacked or stolen by obtaining patient data transmitted via a Bluetooth communications protocol. In other words, wired transmission of corneal topography data is more secure than wireless transmission of corneal topography data. In addition, commands, instructions, signals and messages may be transmitted or communicated between the custom-designed and fabricated mobile communication device 470 and the corneal topography system or housing 407 in order to control other components of the corneal topography system or housing 407.

In some embodiments, the computer-readable instructions 417 may be executable by one or more processors 415 of the topography-specific PCB 412 to control operation of components in the corneal topography system or housing 407 (or corneal topography optical bench). For example, in some embodiments, the one or more processors 415 of the topography-specific PCB 412 may generate commands, instructions or signals to cause the Placido rings (or other illumination pattern) to illuminate, the ranging beam to be generated and transmitted to the patient's eye, the fixation beam to be generated and transmitted to the patient's eye and/or the infrared beam to be generated and transmitted to the patient's eye. Similarly, in some embodiments, the one or more processors 415 of the topography-specific PCB or outboard 412 may generate commands, instructions and/or signals to cause those beams to cease to be generated and/or the Placido rings to be turned off.

In some embodiments, for example, the computer-readable instructions 417 may be executable by one or more processors 415 to generate a signal, command or instruction to a fixation beam assembly 452 to cause the fixation beam assembly 452 to generate a fixation beam (e.g., a green fixation beam) which is transmitted to the patient's eye. Similarly, signals, commands and/or instructions may be generated and communicated to turn off the fixation beam.

In some embodiments, for example, the computer-readable instructions 417 executable by one or more processors 415 may generate a signal, command or instruction to a ranging beam assembly 451 to cause the ranging beam assembly 451 to generate a ranging beam (e.g., a red ranging beam) which is transmitted to the patient's eye. Similarly, signals, commands and/or instructions may be generated and communicated to turn off the ranging beam.

In some embodiments, for example, the computer-readable instructions 417 executable by one or more processors 415 may generate a signal, command or instruction to an infrared light assembly 453 to cause the infrared light assembly 453 to generate an infrared light beam (e.g., an infrared light beam) which is transmitted to the patient's eye. Similarly, signals, commands and/or instructions may be generated and communicated to turn off the infrared light beam.

In some embodiments, for example, the computer-readable instructions 417 executable by one or more processors 415 may generate a signal, command or instruction to a Placido rings controller or circuitry 450 to cause the Placido rings controller 450 to generate signals, commands or instructions to illuminate rings of the Placido rings assembly 410. In some embodiments, the one or more processors may generate a signal, command or instruction directly to a Placido rings assembly 410 to illuminate the Placido rings. Similarly, signals, commands and/or instructions may be generated and communicated to turn off the illumination of the Placido rings in the Placido rings assembly 410.

FIG. 5 illustrates an alternative embodiment utilizing a custom-designed and developed-mobile communication device according to some embodiments. In FIG. 5, the main difference with respect to FIG. 4 is that the camera sensor and potentially the corneal topography software, may be located or resident in the customized-designed and/or fabricated mobile communication device 570. Because the corneal topography system or housing developer is also the developer of the custom-designed and/or fabricated mobile communication device, the developer can control a location or position of the camera sensor and/or lenses in the custom-designed and/or fabricated mobile communication device and thus will not have the variations that are present in other phone manufacturer's cameras and lenses (e.g., Apple, Samsung, Motorola, Google). Thus, the custom-designed mobile communication device camera may be located at a horizontal center of the custom-designed mobile communication device and may receive the reflected Placido rings image via the image path 530. Because the corneal topography system developer controls and/or has customized both pieces (e.g., the custom-designed and fabricated mobile communication device 570 and the corneal topography system and housing 507), tight tolerances may be maintained with the optical components in both devices. In addition, the developer will also control the custom-designed and developed mobile communication device operating system and/or the corneal topography system operating system, so unexpected driver updates (and potentially problematic updates) for components of either system (e.g., the custom-designed mobile communication device and/or the corneal topography system or housing) will not be an issue. In some embodiments, the topography-specific PCB or outboard that was disclosed in FIG. 4A may be eliminated in FIG. 5. In some embodiments, the custom-designed and/or fabricated mobile communication device 570 may communicate commands, signals and/or instructions with the corneal topography system or housing 507 via a wired communication interface or communication circuitry 526 (e.g., a USB-3 interface) utilizing a cable 527 and the wired communication interface or communication circuitry 525 in the corneal topography system or housing 507. Alternatively, the custom-designed and/or fabricated mobile communication device 570 may communicate commands, signals and/or instructions with the corneal topography system or housing 507 utilizing a wireless communication interface 526 such as Bluetooth or Wi-Fi without the need of a physical cable. In some embodiments, the custom-designed mobile communication device communication interface or communication circuitry (whether wired or wireless) may control operations of components in the corneal topography system or housing 507, such as the fixation light source 552, the infrared light source 553, the ranging light source 551 and/or the Placido rings illumination assembly (or other pattern illumination system) 510. In some embodiments, computer-readable instructions 517 stored in one or more memory devices 516 and executable by the one or more processors 515 in the custom-designed mobile communication device 570 may perform image processing of the reflected Placido rings image or other illuminated pattern image (the operations or which were described previously). In other words, in FIG. 5, the corneal topography application software would be stored and executed by one or more processors on the custom-designed mobile communication device.

Figure 6A:
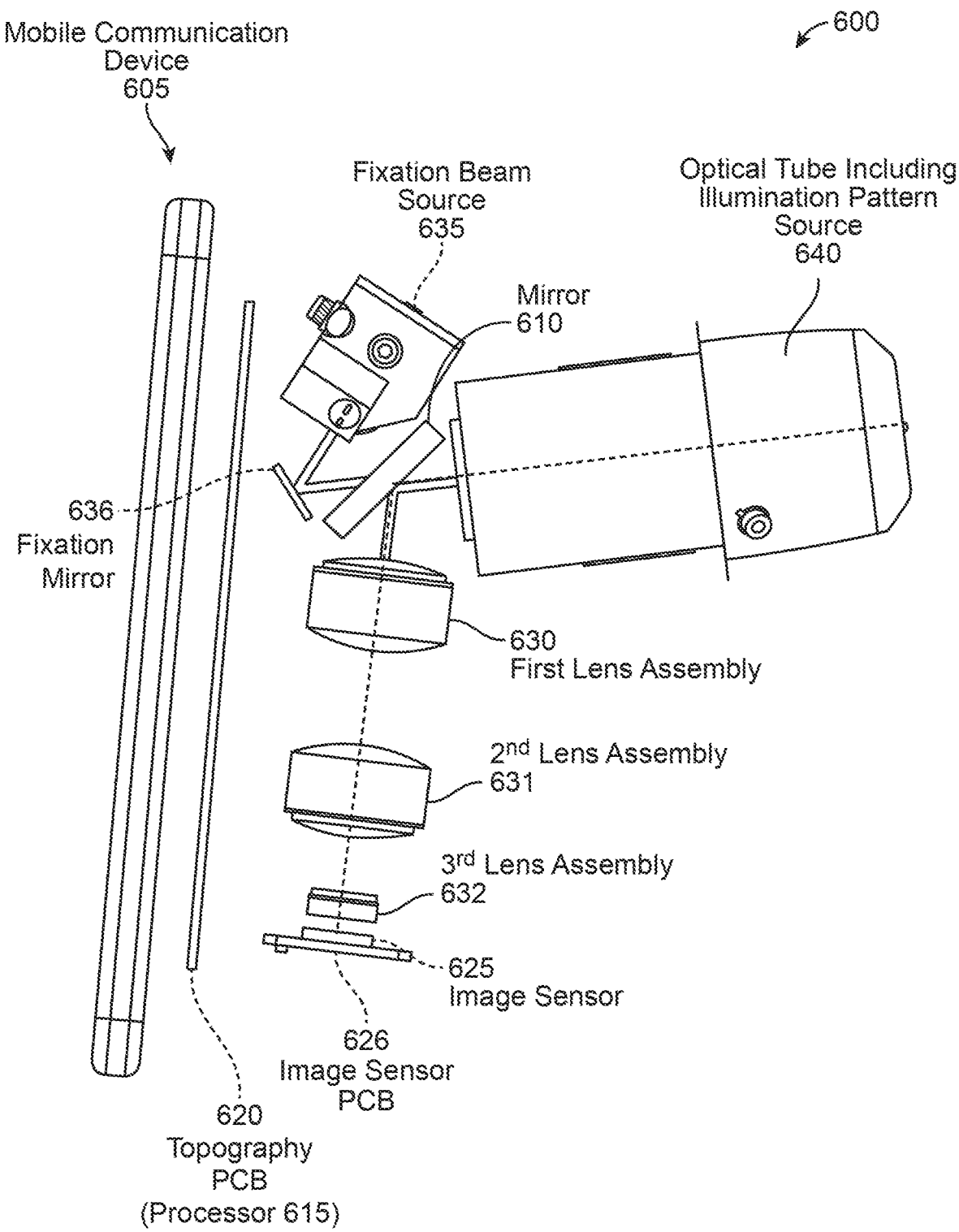
FIG. 6A illustrates a side view of components of a mobile communication device-based corneal topography system according to some embodiments.

FIG. 6A illustrates a side view of components of a mobile communication device-based corneal topography system according to some embodiments. In some embodiments, the mobile communication device-based corneal topography system 600 may comprise a mobile communication device 605; a topography processor 615 and/or a topography printed circuit board 620; an image sensor 626 and/or an image sensor printed circuit board 626; one or more lens assemblies (e.g., a first lens assembly 630, a second lens assembly 631, and/or a third lens assembly 632), a mirror 610, and/or an optical tube that includes an illumination pattern source 640. In some embodiments, the mobile communication device-based corneal topography system 600 may further comprise a fixation beam source 635 and/or a fixation mirror 636. In some embodiments, the mobile communication device-based corneal topography system 600 may further comprise a ranging beam source 710 and/or one or more proximity sensors 720 (both illustrated in FIG. 7A). In some embodiments, the mobile communication device 605 may comprise a mobile communication device display 606.

There is a significant advantage to moving to a mobile-communication device-based corneal topography system having an image sensor and/or topography processing hardware and/or software outside of the mobile communication device (which may be referred to as outboard). All mobile communication device (e.g., smartphone) cameras or sensors have their own integrated lens systems with auto-focus and zoom. These features are not needed in the corneal topography system and if the mobile communication device camera was utilized as the sensor in the corneal topography system, these features would need to be disabled and/or a work around would need to be developed. In addition, all mobile communication device cameras incorporate infrared and/or far red filters to eliminate "red eye" in photos. The corneal topography system described and claimed herein desired to eliminate this filter (infrared and/or far red) and instead utilize the red light and infrared spectrum for pupil edge detection, and potentially autorefraction. In addition, even in high end name-brand mobile communication devices such as Apple iPhone and Android phones, there are very tiny differences in spacing of the mobile communication device lens(es) from the image sensor or camera. For corneal topography features, if the mobile communication device camera is utilized, these very tiny differences would need to be measured, recorded and/or factored in calibration for each and every instrument (e.g., mobile communication device-based corneal topography system). Having to measure, record and factor these very tiny differences for each mobile communication device would be clunky, cumbersome, undersireable and costly in a production context. Thus, by utilizing an image sensor outside the mobile communication device, the image sensor may be bonded to the optical bench (which includes all of the lensing elements (e.g., lens)) so that the spacing for each instrument is uniform, reproducible and/or consistent. In addition, by not having to guide the reflected image of the illumination pattern through a mobile communication device lens system, the configurations described herein is optimized so that a design of the imaging system for imaging the reflected illumination pattern of the cornea to the dedicated image sensor.

In some embodiments, the image sensor 625 may communicate with the topography processor 615) and/or other components on a topography PCB 620 via an interface, such as a MIPI interface. In some embodiments, the corneal topography system may comprise a battery or power source (e.g., such as a lithium ion battery) that is included in a housing. In some embodiments, the topography processor may be configured with instructions to communicate with other components or assemblies within a housing or the mobile communication device-based corneal topography system 600 such as one or more thermal or temperature sensors (not shown), a fixation beam source 635, the illumination source (or illumination pattern source) 640, the ranging beam source 710, and/or an infrared light source (shown in FIG. 3). In some embodiments, the illumination pattern source 640 may comprise two parts. In some embodiments, the illumination system may be referred to as an illumination pattern source. In some embodiments, the illumination system 641 may generate an illumination pattern that is reflected of a cornea of a subject or patient. In some embodiments, an imaging system may be coupled to the illumination system and coupled to an image sensor. In some embodiments, the imaging system may direct the reflected illumination pattern to the image sensor. In some embodiments, the image sensor 625 may capture an image of the reflected illumination pattern. An important advantage of the embodiments described in FIGS. 6A, 6B, 7A and 7B is that the image sensor 625 may be located in an optical housing and is separate from an image sensor or camera in the mobile communication device 605. As described previously, including the image sensor in a housing with the imaging system allows a fixed alignment of the image sensor 625 and the imaging system. In addition, it eliminates the mobile communication device-based corneal topography system having to identify and/or address the different characteristics and specifications of the image sensors in the mobile communication device, as well as potential different mobile communication device image sensor locations.

In some embodiments, the mobile communication device-based corneal topography system may further comprise an interface. In some embodiments, the interface may be the Mobile Industry Processor Interface (or MIPI interface) (not shown). In some embodiments, the MIPI interface may be coupled to the image sensor 625 and/or the topography processor 615. In some embodiments, the image sensor 625 may be configured with instructions to communicate, via the MIPI interface, the captured images of the reflected illumination pattern to the topography processor 615. In some embodiments, the topography processor 615 may be configured with instructions to communicate the captured image of the reflected illumination pattern to the mobile communication for presentation on the display of the mobile communication device 605 to allow for viewing by the Examiner. In some embodiments, the communication of the reflected illumination pattern image to the mobile communication device may occur in real time. In some embodiments, the topography processor 615 may be configured with instructions to control operation of the image sensor (e.g., to specify parameters or measurements of the image captured by the image sensor 625). In some embodiments, the topography processor 605 may communicate commands or instructions to the image sensor 625 to control a size, a resolution and/or a frequency of when an image is refreshed or recaptured (which may be referred to as a frame rate). In some embodiments, the topography processor may communicate instructions to the image sensor 625 to down-size an image. For example, for the auto-capture process described above and below, a high resolution (e.g., 3K×3K) may be utilized for the image being evaluated in the auto-capture process whereas for a topography process (e.g., rings analysis process that is described below), a smaller resolution (e.g., 1K×1K) of the captured image of the reflected illumination pattern may be utilized. During the auto-capture process, the topography processor 615 may be configured with instructions to enable or set different regions of interest in the reflected image of the fixation beam and/or the ranging beam. In this embodiment, then the topography processor 615 may only be evaluating a center area of the reflected image of the fixation beam and/or the ranging beam to find and determine overlap of the fixation beams and the ranging beam. In this embodiment, this may allow the corneal topography system described herein to utilize a higher frame rate to achieve auto-capture and/or also to utilize a higher resolution image at that frame rate.

In some embodiments, a topography processor 615 may be configured with instructions to process the image of the reflected illumination pattern to generate topography map images and/or one or more topography data files. In some embodiments, the topography data files may include 1) ring edge location measurements, 2) calibration data, 3) patient identifier data and/or 4) x, y and/or z-axis offset data. In some embodiments, the topography processor 615 may be configured with instructions to communicate the generated topography map images and the one or more data files to the mobile communication device 605. In some embodiments, a processor on the mobile communication device 605 may be configured with instructions to present the generated one or more topography map images on a display of the mobile communication device.

In some embodiments, the mobile communication device-based corneal topography system may utilize an auto-capture process to verify that accurate positioning in the x, y and z-axis of a cornea (of the subject) is present as the reflected illumination pattern is captured. In some embodiments, the pattern illumination source or component 640 may not be initially illuminated. In some embodiments, the pattern illumination source or component 640 may be illuminated. In some embodiments, a fixation beam source 635 may generate a fixation beam which may travel on a fixation path which forms fixation axis (which has two portions 655 and 656). In some embodiments, the fixation beam defines a fixation target visible to the eye of the subject, the fixation target beam comprising a first wavelength of light. In some embodiments, a ranging beam source 710 may generate a ranging beam 715 and direct the ranging beam to the cornea of the subject. In some embodiments, the ranging beam 715 may also be referred to an alignment beam and the ranging beam source 710 may be referred to as an alignment beam source. In some embodiments, the ranging beam 715 may comprise a second wavelength of light that is different from a first wavelength of light. In some embodiments, the ranging beam 715 may travel along a path which may be referred to as a ranging axis. In these embodiments, the image sensor 625 may capture a reflected image of a ranging beam and a fixation beam on the cornea of the subject. In some embodiments, as shown an angle between the fixation axis (beam) and the imaging axis (beam) is illustrated by reference number 716.

In these embodiments, the image sensor 625 may be configured with instructions to communicate the reflected image of the ranging beam and the fixation beam to the topography processor 615 via the interface. In these embodiments, the topography processor 615 may communicate the reflected image of the alignment beam and the fixation beam to the mobile communication device 605 to display on the mobile communication device display 616 and to allow the examiner to move the corneal topography system. In some embodiments, multiple frames of the reflected image of the fixation beam and the ranging beam may be communicated from the image sensor 625 to the topography processor 615. In some embodiments, the one or more frames of the reflected image of the fixation beam and the ranging beam may be communicated from the topography processor to the mobile communication device 605. In some embodiments, the one or more frames of the reflected image of the fixation beam and the ranging beam may include a mark or cross hair (e.g., a fiducial mark) which may be utilized to identify a center of an overlap of the fixation beam and the ranging beam by the operator (e.g., the examiner) of the mobile communication device-based corneal topography system. In other words, the mark or cross-hair (e.g., yellow cross-hairs) facilitate proper alignment, by providing visual cues to the person performing the topography exam. In some embodiments, a process of centering the ranging and fixation beams may require operator guidance of steering the mobile communication device-based corneal topography system when mounted on the slit lamp microscope so as to achieve an optical position of the fixation and ranging beam within the yellow cross-hairs.

In these embodiments, the topography processor 615 may be configured with instructions to determine if the ranging beam and the fixation beam are overlapping. In these embodiments, for example, the topography processor 615 may be configured with instructions to determine the beams are overlapping by tracking the first wavelength of light (e.g., the fixation beam) and the second wavelength of light (e.g., the ranging beam) with spectral analysis. In some embodiments, the topography processor 615 may also be configured with instructions to verify that an overlap of fixation beam and the ranging beam are in alignment with a fiducial mark or cross-hairs in the reflected image of the fixation beam and the ranging beam (the cross-hairs may be yellow cross-hairs in order to stand out or be distinct from a red ranging beam and green fixation beam). In some embodiments, the operator or user may move the fiducial mark or cross-hairs by moving the mobile communication device-based corneal topography system 600 utilizing the joystick or similar device on the slit lamp microscope (to which the system 600 is mounted). If the topography processor 615 determines that these conditions have been met (e.g., beams overlapping and aligned with fiducial mark or cross-hairs), the topography processor 615 may be configured with instructions to turn off or deactivate the fixation beam source 635 and/or the ranging beam source 710. In other words, the topography processor 615 may send shutdown or deactivation commands or instructions to the fixation beam source 635 and/or the ranging beam source 710.

In some embodiments, once it is determined that the fixation beam and the alignment beam are overlapping each other, the topography processor 615 may be configured with instructions to instruct, command or signal the pattern illumination component or source 640 to turn on and/or illuminate in order to project the illumination pattern onto the cornea of the subject. In some embodiments, the pattern illumination component or source 640 may already be illuminated and thus be projecting an illumination pattern on a cornea of the subject. In these embodiments, the topography processor 615 may be configured with instructions to command, instruct and/or signal the image sensor 625 to capture a reflected illumination pattern image. In these embodiments, the image sensor 625 may be configured with instructions to automatically capture the reflected illumination pattern image and to communicate the captured reflected illumination pattern image to the topography processor 615. In other words, no human intervention may be required in performing these steps. The auto-capture process described herein is an advantage over prior art systems where multiple tests have to be performed in order to an image of acceptable quality. This auto-capture process helps reduce human error in capturing images of the reflected illumination pattern at the correct corneal vertex. This auto-capture process will speed up examinations of subjects and improve the quality and accuracy of the captured images, as well as the topography map images and the one or more topography data files generated therefrom.

In these embodiments, the image sensor 625 may be configured with instructions to communicate, via the interface, the captured reflected illumination pattern image to the topography processor 615 for topography processing. In these embodiments, the topography processor 615 on a topography PCB 620 may be configured with instructions to perform topography processing and to generate one or more topography map images and one or more topography data files. In some embodiments, the topography processor 615 may be configured with instructions to communicate the generated one or more topography map images and the one or more topography data files to the mobile communication device 605. In some embodiments, the topography processor may also communicate the captured image of the reflected illumination pattern (or some derivative thereof) to the mobile communication device 605. In some embodiments, the processor of the mobile communication device 605 may be configured with instructions to present the one or more topography map images on the display 606 (either by themselves or with the reflected illumination pattern image (e.g., the captured reflected illumination pattern image)). In some embodiments, the processor of the mobile communication device 605 may be configured with instructions to communicate the reflected illumination pattern image (or a derivative thereof) and/or the one or more topography data files to a cloud-based server and/or remote computing device for storage and/or analysis.

In some embodiments, the communication of 1) reflected illumination pattern images; 2) one or more topography map images; and 3) one or more topography data files to the mobile communication device may occur utilizing a wired communication interface. In some embodiments, the wired communication interface may operate according to the USB-2 and/or the USB-3 communication protocol (although other communications protocol may be utilized). In some embodiments, the wired communication interface may be a USB-2 and/or USB-3 cable. The utilization of the wired communication interface provides protection from outside individuals being able to access and/or hack the reflected illumination pattern images, the topography map images and/or the one or more topography data files as they are being transferred to the mobile communication device. This protection is a significant advantage over other systems as it provides protection for subject's personal health-related data. In some embodiments, the mobile communication device 605 may utilize one or more wireless communication transceivers to communicate the reflected illumination pattern image (or derivative thereof) and the one or more topography data files to a cloud-based server and/or remote computing device. In some embodiments, the one or more wireless communication transceivers may be transceivers operating according to any one of a number of 802.11 protocols, WiFi transceivers and/or wireless LAN protocols. In some embodiments, the one or more wireless communication transceivers may be cellular transceivers which operate according to the 3G, 4G and/or 5G communication transceivers. In some embodiments, the one or more wireless communication transceivers may be personal area network transceivers (e.g., Zigbee, Bluetooth, and/or Bluetooth Low Energy transceivers, or potentially NFC transceivers).

In some embodiments, the topography processor 615 on a topography PCB 620 may be configured with instructions to perform multiple steps as part of the topography processing of the captured image of the reflected illumination pattern. Below is a representative example of different steps in topography processing. However, slight variations to the steps or process described below (for topography processing) may be utilized with the claimed subject matter. In an embodiment, for example, the topography processor 615 may be configured with instructions to find and/or locate centroids of central rings of the reflected illumination pattern and then utilize the centroids data to determine a position of a vertex normal for the cornea being analyzed. In this embodiment, for example, the topography processor 615 may be configured with instructions to calculate and/or determine other data (e.g., such as x-y-z offset data from a perfect position). In this embodiment, the x-y-z offset data may be utilized as an indicator of test accuracy and/or reliability. In other words, the x-y-z offset data may be thought of as any decentration, pitch or yaw of the corneal apex from the expected position.

In this embodiment, for example, the topography processor 615 may be configured with instructions to 1) find and/or determine ring edge locations and/or 2) represent these ring edge location in polar coordinates, through 360 degrees of arc in 1-degree increments for all rings of the captured image of the reflected illumination pattern. In this embodiment, for example, if there are 28 rings in the image of the reflected illumination pattern, that means there are 56 ring edges.

In this embodiment, for example, a topography processor 615 may be configured with instructions to create a topography data file or one or more topography data files. In some embodiments, the topography data file may comprise data representative of ring edge locations (e.g., the polar coordinates described above), calibration reference data, patient identifier data and/or right eye/left eye data. In some embodiments, the topography data file may further comprise x-y-z offset data and/or vertex normal data. In some embodiments, the topography data file may be more than a single file and may be referred to as one or more topography data files.

In this embodiment, for example, the topography processor 615 may be configured with instructions to 1) analyze the topography data file (or the one or more topography data files) and 2) generate topography power maps (or topography map images) along with statistical data and derivative analyses data (which is based upon the statistical data). In some embodiments, the one or more topography data files described above may further comprise the statistical data and/or the derivative analysis data.

In some embodiments, other components and/or assemblies (e.g., memory devices (volatile and/or non-volatile), controllers, flash memories, etc.) on a topography PCB 620 may assist the topography processor 615 in performing the below listed operations. Although the topography PCB 620 is described as a single printed circuit board, multiple printed circuit boards and/or chipsets may be utilized to perform the functions identified as being performed by the topography PCB 620. Although the topography processor is described as a single processor, multiple processors and/or chipsets may be utilized to perform the functions identifier as being performed by the topography processor 615. In addition, in some embodiments, the topography PCB 620 may also comprise one or more interfaces to communicate with other components or assemblies within the mobile communication device-based corneal topography system.

Figure 6B:
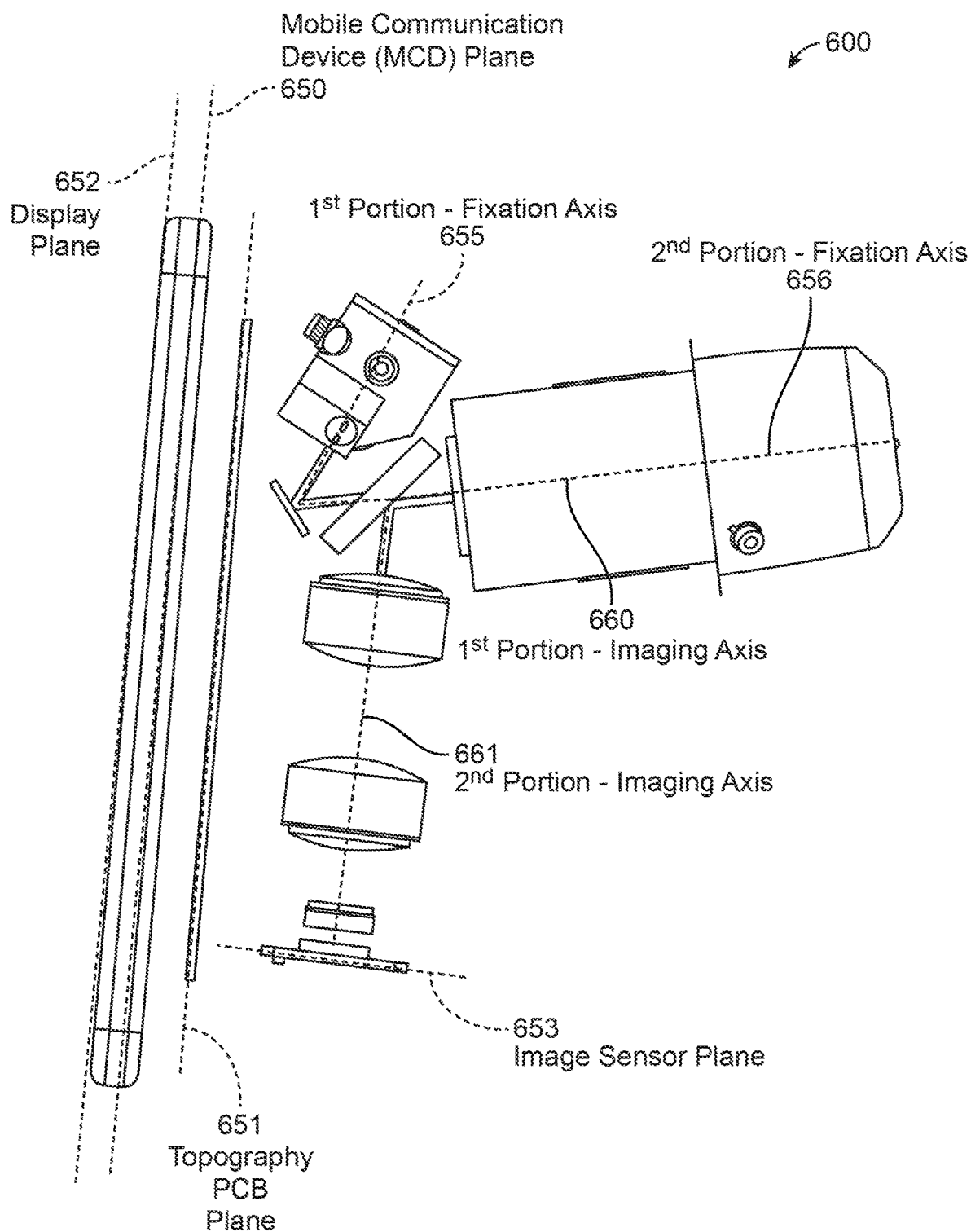
FIG. 6B illustrates relationships of a number of planes and axes in a mobile communication device-based corneal topography system according to some embodiments.

FIG. 6B illustrates axis' and/or planes in a mobile communication device-based corneal topography system according to some embodiments. In some embodiments, the mobile communication device-based corneal topography system 600 may comprise an imaging system. In some embodiments, the imaging system may comprise one or more lens assemblies (e.g., lens assemblies 630, 631 and 632), the optical tube including the illumination pattern source 640 (which may be a Placido rings illumination source), the mirror 610 (or beam mirror) and the image sensor 625. In some embodiments, the illumination pattern source 640 may generate an illumination pattern and cause an illumination pattern to be reflected off a subject's cornea. In some embodiments, the reflected illumination pattern may be reflected off the mirror 610 through one or more lens assemblies (e.g., lens assemblies 630, 631 and 632) to the image sensor 625. In some embodiments, the path travelled by the reflected illumination pattern of the subject's cornea may be referred to as the imaging axis or imaging path. In some embodiments, the imaging axis may also be referred to as the optical axis. In some embodiments, a first portion of the imaging axis 660 may extend from the subject's cornea to the mirror 610. In some embodiments, a second portion of the imaging axis 661 may extend from the mirror 610 to the imaging sensor 625. In some embodiments, the one or more lens assemblies (e.g., lens assemblies 630, 631 and 632) may be positioned along the second portion of the imaging axis 661 or the optical axis to image the reflected illumination pattern so as to fit a size of the image sensor 625. In some embodiments, the one or more lens assemblies may be positioned along the second portion of the imaging axis 661 or the optical axis to image the reflected illumination pattern at a magnification so as to fit a size of the image sensor 625, and wherein the magnification is between 0.25 to 0.75, optionally 0.35 to 0.65, or optionally 0.45 to 0.55. In some embodiments, the one or more lens assemblies may be positioned along the second portion of the imaging axis 661 to image the reflected illumination pattern at a magnification so as to fit a size of the image sensor, wherein the magnification may be between 0.75 to 1 or alternatively greater than 1. With the single mirror configuration disclosed in FIG. 6A and FIG. 6B, the corneal topography system may fold the imaging beam path (or imaging axis), which shortens an otherwise uncomfortably long image path or imaging axis so that it can be utilized in the slit-lamp mounted context. This preserves the relative position that is normally occupied by the examiner and the patient on either side of the slit lamp during an examination.

In some embodiments, the optical path extending from the subject's cornea to mirror 610 may be referred to as a first portion of the optical axis. In some embodiments, the optical path extending from the mirror 610 through the one or more lens assemblies and to the image sensor 625 may be referred to as a second portion of the optical axis. In some embodiments, the optical axis may be aligned with the imaging axis.

In some embodiments, the topography processor 615 may be supported by a topography printed circuit board (PCB) 620. In some embodiments, the topography printed circuit board 620 may be inclined at an angle with respect to vertical. In some embodiments, the topography PCB may extend along a topography PCB plane 651. In some embodiments, the mobile communication device (MCD) 605 may be inclined at an angle with respect to a vertical axis. In some embodiments, the mobile communication device 605 may comprise an MCD printed circuit board supporting an MCD processor. In some embodiments, the mobile communication device may extend along an MCD plane 650. In some embodiments, the display 606 of the mobile communication device 605 may be inclined with respect to a vertical axis. In some embodiments, the display 606 may extend along a display plane 652. In some embodiments, the image sensor 625 may be supported by an image sensor PCB 626. In some embodiments, the image sensor PCB 626 may extend along an image sensor plane 653.

In some embodiments, the mobile communication device 605 may further comprise one or more memory devices, one or more wireless communication transceivers, one or more near-field communication (NFC) transceivers, one or more Global Positioning System (GPS) transceiver or receivers, and/or one or serial communication transceivers and/or interfaces. In some embodiments, a number of the above-mentioned components may be supported, coupled and/or attached to an MCD printed circuit board.

Figure 7A:
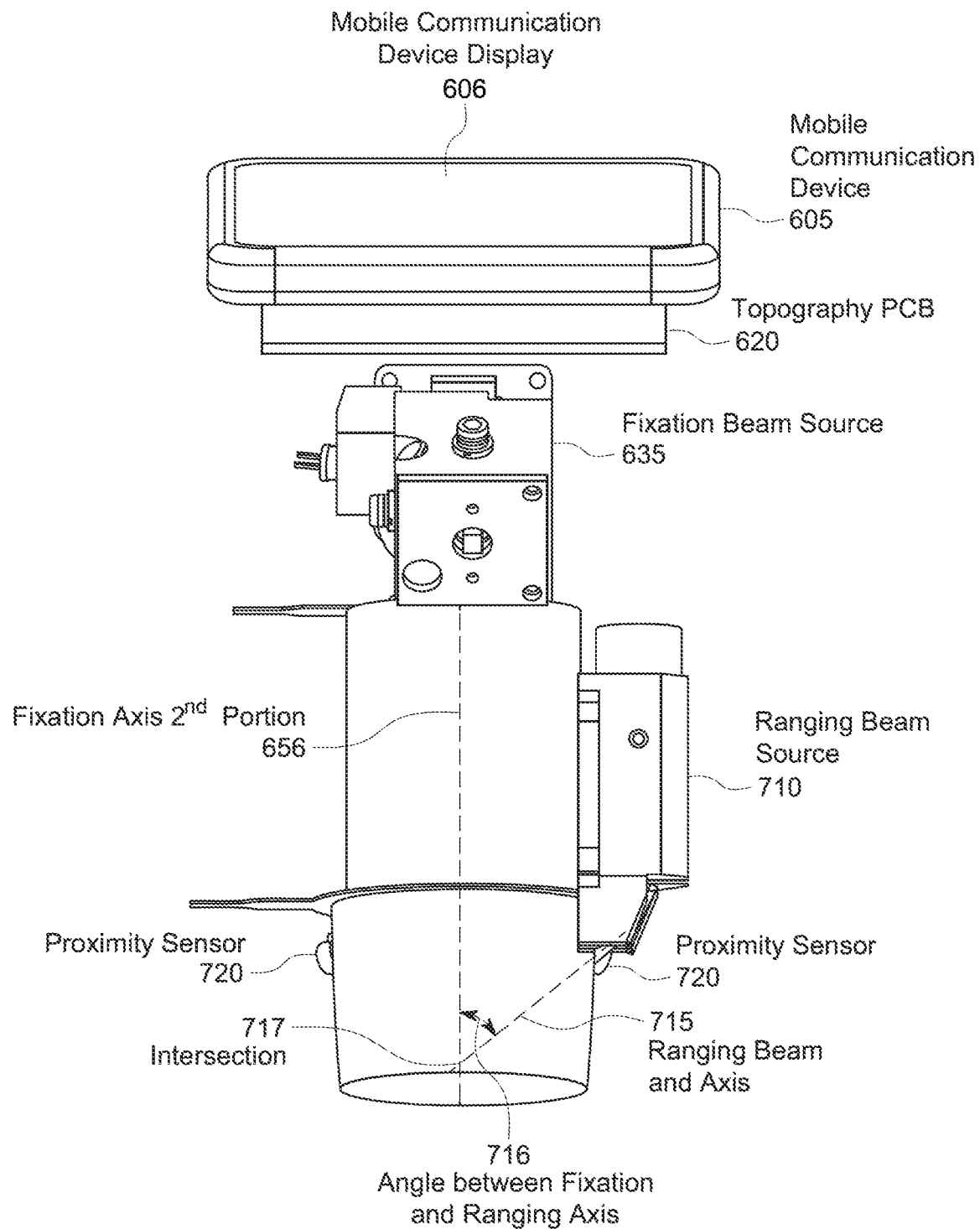
FIG. 7A illustrates a top view of components and assemblies of a mobile communication device-based corneal topography system according to some embodiments.
Figure 7B:
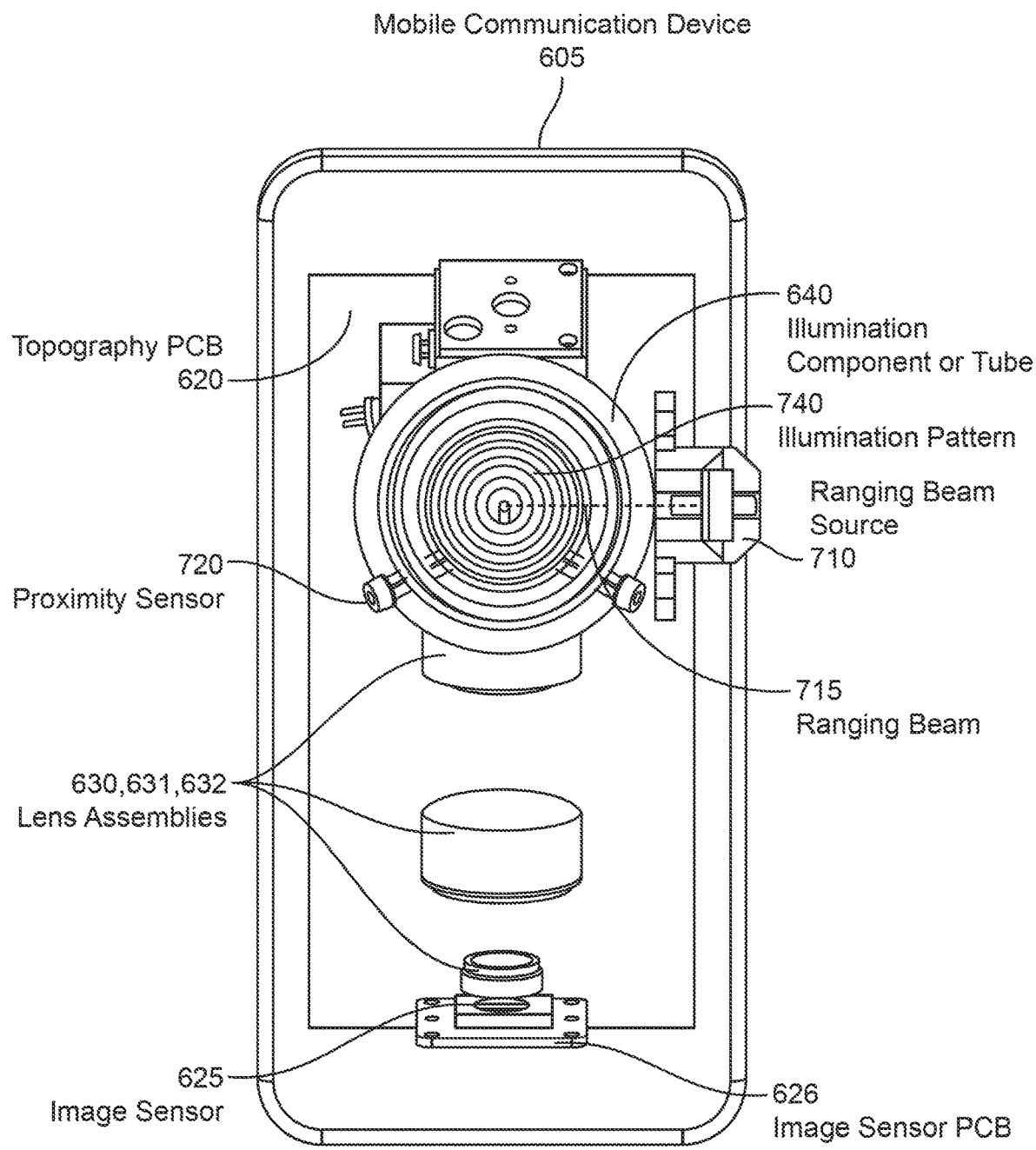
FIG. 7B illustrates a front view of components and assemblies of a mobile communication device-based corneal topography system according to some embodiments.

FIG. 7A illustrates a top view of components and assemblies of a mobile communication device-based corneal topography system according to some embodiments. FIG. 7B illustrates a front view of components and assemblies of a mobile communication device-based corneal topography system according to some embodiments. In some embodiments, the imaging system of the mobile communication device-based corneal topography system may include a fixation beam source 635 to generate a fixation beam, the fixation beam defining a fixation target visible to the eye of the subject. In some embodiments, the fixation target beam may comprise a first wavelength of light. In some embodiments, a ranging beam source 710 may generate a ranging beam 715, the ranging beam 715 comprising a second wavelength of light and the second wavelength of light may be different from the first wavelength of light. In some embodiments, the ranging beam 715 may travel along a ranging axis. In some embodiments, an angle between the fixation beam and the ranging beam 716 may be illustrated as 716 in FIG. 7A.

In some embodiments, the image sensor 625 may be configured to image a reflection of the fixation beam and the ranging beam from the cornea of the subject and communicate the image of the reflection of the fixation beam and the ranging beam to the topography PCB 620 (via an interface). In some embodiments, the topography processor 615 on a topography PCB 620 may be configured with instructions to determine when the fixation beam and the ranging beam are overlapping (e.g., as discussed in detail above and as illustrated in FIGS. 1 and 2). In some embodiments, when the fixation beam and the ranging beam are found to be overlapping, the topography processor 615 may be configured with instructions to turn off the fixation beam source and the ranging beam source. The fixation beam source and the ranging beam source may be turned off or deactivated to eliminate those beams from the reflected illumination pattern. In some embodiments, the topography processor 615 may be configured with instructions to instruct, command or cause the image sensor 625 to automatically capture an image of the reflected illumination pattern. As discussed previously, the overlapping of the fixation beam and alignment beam allows the image sensor 625 to automatically capture the reflected illumination pattern at the correct corneal vertex.

In some embodiments, the ranging beam 715 may travel along a ranging axis and the fixation beam may travel along a fixation axis 656 (e.g., a second portion of the fixation axis 656) and there may be an intersection (as illustrated by reference number 717 in FIG. 7A). In some embodiments, the ranging axis may be at an angle 716 with respect to the fixation axis 656 within a range of 25 to 65 degrees, optionally 40 to 60 degrees and optionally 45 degrees. In some embodiments, because an intersection may involve two beams (e.g., the fixation beam and the ranging beam), the intersection 717 may not be a point but more a spot or area or intersection as shown previously in FIGS. 1A, 1B and 2.

In some embodiments, the image sensor 625 may comprise an array of pixels, the array comprising a first plurality of pixels more sensitive to the first wavelength than the second wavelength and a second plurality of pixels more sensitive to the second wavelength than the second wavelength. In some embodiments, the first wavelength may comprise a first color and the second wavelength may comprise a second color different from the first color. In some embodiments, the MCD processor may be configured with instructions to display a portion of the reflected fixation beam and the reflected ranging beam on a display 606 of the mobile communication device 605. In some embodiments, the MDC processor may be configured with instructions to display where the first beam overlaps with the second beam with a different color than the first wavelength and the second wavelength. In some embodiments, the ranging beam may be configured to overlap with the fixation beam at a vertex of the cornea.

In some embodiments, the fixation beam may comprise substantially collimated light prior to reflection off the subject's cornea. In some embodiments, the image of the fixation beam from an anterior surface of cornea may comprise a maximum size across within a range from about 10 um to about 1 mm. In some embodiments, the fixation beam may be collimated to within about 5 degrees. In some embodiments, the ranging beam may be focused to the waist at a full cone angle within a range from about 1 degree to about 45 degrees. In some embodiments, the ranging beam 715 may comprise an image of scattered light from the cornea when a tear film covers the cornea and optionally wherein the scattered light comprises light scattered from Bowman's membrane or corneal stroma of the eye beneath the tear film.

In some embodiments, the mobile communication device-based corneal topography system 600 may further comprise a fixation beam source 635 and a fixation mirror 636. In some embodiments, the fixation beam source 635 may generate a fixation beam or fixation light beam which may travel along a fixation path or fixation axis. In some embodiments, a fixation axis or fixation path may include a first portion 655 and a second portion 656, although in other embodiments the fixation path or fixation axis may include one portion or more than two portions. In some embodiments, as illustrated in FIG. 6B, a first portion 655 of a fixation axis or path may be from the fixation beam source 635 to the fixation mirror 636. In some embodiments, as illustrated in FIG. 6B, a second portion 656 of the fixation axis or path may be from the fixation mirror 636 to the cornea of the subject or patient. In some embodiments, as illustrated in FIG. 6B, the second portion of the fixation axis 656 may be aligned and/or coaxial with a first portion of the imaging axis 660.

In some embodiments, the fixation beam source 635 may transmit a fixation beam to the fixation mirror 636. In some embodiments, the fixation beam is reflected from the fixation mirror 636 to a mirror 610 and onto to the cornea of the subject being examined. In some embodiments, the mirror 610 may be a dichroic mirror that transmits the fixation beam along a second portion 656 of the fixation axis to the cornea of the subject. In some embodiments, the dichroic mirror may also transmit (and not reflect) the infrared beam utilized in pupil edge detection to the cornea (as discussed with respect to FIG. 3). In some embodiments, the dichroic mirror may reflect the reflected illumination pattern or the reflected image of the alignment beam and/or the fixation beam to the image sensor 625. In other words, the mirror 610 may be a partial transmittance, partial reflectance mirror where certain wavelengths are transmitted through the mirror, whereas other wavelengths are reflected off the mirror 610. In some embodiments, the mirror 610 may be positioned or have an angle of inclination of approximately 135 degrees with respect to the second portion of the fixation axis 656 (when being viewed from the fixation mirror 636). Alternatively, in some embodiments, the mirror 610 may have an angle of inclination with respect to the second portion 656 of the fixation axis in a range of 95 to 175 degrees, optionally 110 to 160 degrees, or optionally 125 to 145 degrees.

In some embodiments, as is illustrated in FIG. 7B, the mobile communication device-based corneal topography system 600 comprises an optical tube or illumination source component 640 and a ranging beam source 710. In some embodiments, the ranging beam source 710 may be coupled or connected to an outside surface of the optical tube or illumination source component 640. In some embodiments, the optical tube or illumination source component 640 may include an opening, where the opening extends from the outside surface of the optical tube 640 to the inside surface of the optical tube to define an aperture therebetween. In these embodiments, the ranging beam source 710 may transmit the ranging beam 715 through the aperture to the cornea of the subject. In some embodiments, the ranging beam source 710 may be coupled to the outside surface of the optical tube 640 at a position between 1 o'clock and 5 o'clock with respect to vertical, optionally between 2 o'clock and 4 o'clock, or optionally at 3 o'clock with respect to vertical.

In some embodiments, a housing (which may be referred to as an optical housing) may enclose the illumination system 641, the imaging system (including the image sensor 625) and the topography processor 615 (and/or the topography printed circuit board (PCB) 620). In other embodiments, the housing may also enclose the mobile communication device 605. In other embodiments, the housing may partially enclose the illumination system 641, the imaging system (including the image sensor 625) or the topography processor 615 (and/or the topography printed circuit board (PCB) 620). In these embodiments, the housing may further partially enclose the mobile communication device 620. In other words, the mobile communication device-based corneal topography system 600 described herein may include a housing that has different combinations of components and/or assemblies that are enclosed and/or covered by the housing.

Figure 8:
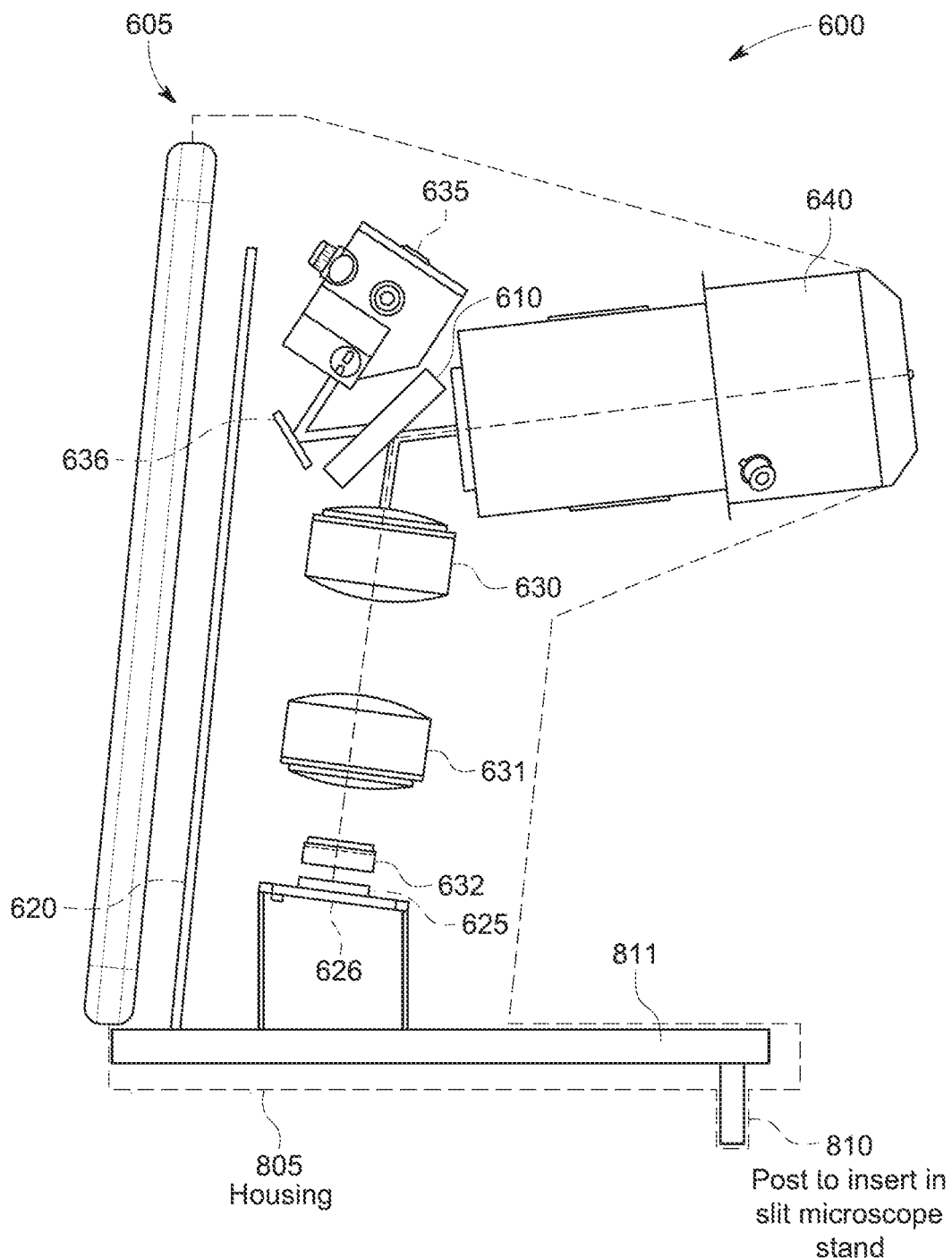
FIG. 8 illustrates a side view of a mobile communication device-based corneal topography system including a housing according to some embodiments.

FIG. 8 illustrates a side view of a housing enclosing portions of the mobile communication device-based corneal topography system 600 according to embodiments. In some embodiments, as illustrated by FIG. 8, the housing 805 may enclose the illumination pattern source, the imaging system, e.g., mirror 610, fixation mirror 636, fixation beam source 635, lens assemblies (e.g., 630, 631, 632), the image sensor 626 and the image sensor PCB 626, the topography processor 615 and the topography PCB 620. In some embodiments, the housing 805 is coupled to a post 810 or assembly to insert into the slit-lamp microscope stand in order to mount the mobile communication device-based corneal topography system 600 to the slit-lamp microscope. In the embodiment illustrated in FIG. 8, the mobile communication device 605 may be attached or mounted to a side of the housing 805 or may be partially enclosed by the housing 805. FIG. 8 is an illustrative embodiment of the housing of the mobile communication device-based corneal topography system 600 and many other configurations may be utilized with the subject matter described herein. In some embodiments, certain assemblies or components or devices or boards may be partially enclosed by a housing, and in other embodiments, certain assemblies, components, devices or boards may be attached to the housing 805.

In some embodiments, the post 810 is coupled to a support 811, which is configured to support the housing 805 and internal components within the housing. In some embodiments, the housing 805 is configured to be removed while post 810 and support 811 support the internal components, in order to allow alignment and servicing of the topography system. The support 811 may comprise any suitable structures to support the internal components. In some embodiments, the support is coupled to and supports the imaging system, e.g., mirror 610, fixation mirror 636, fixation beam source 635, lens assemblies (e.g., 630, 631, 632), the image sensor 626 and the image sensor PCB 626, the topography processor 615 and the topography PCB 620. The support may comprise one or more of extensions, rails, plates, optical mounts, rails or other structures to support the mobile communication device-based corneal topography system 600 with post 810 in order to allow the topography system to couple to a slit lamp base and pivot as described herein.

In the Figures presented herein, the components and/or assemblies of the mobile communication device-based corneal topography system are configured in specific alignments in order to efficiently utilize space in the housing, in accordance with some embodiments. Other embodiments, may have different alignments and/or spacing the components assemblies and/or devices of the mobile communication device-based corneal topography system as described herein.

Referring again to FIGS. 6A and 6B, in some embodiments, an angle of inclination of a display plane 652 may be within 20 degrees of an angle of inclination of the topography PCB plane 651, optionally within 10 degrees of an angle of inclination of the topography PCB plane 651, or optionally parallel with an angle of inclination of the topography PCB plane 651. In some embodiments, an angle of inclination of a mobile communication device plane (MCD plane) 650 may be within 30 degrees of an angle of inclination of the topography PCB plane 651, optionally within 10 degrees of an angle of inclination of the topography PCB plane 651 or optionally parallel with an angle of inclination of the topography PCB plane 651. In some embodiments, an angle of inclination of the image sensor plane 653 with respect to the topography PCB plane 651 may be within a range from 45 degrees to 135 degrees, optionally from 75 degrees to 105 degrees, optionally from 85 degrees to 95 degrees, optionally at an oblique angle, or optionally perpendicular. In some embodiments, an angle of inclination of the image sensor plane 653 with respect to the display plane 652 may be within a range from 45 degrees to 135 degrees, optionally from 75 degrees to 105 degrees, optionally from 85 degrees to 95 degrees, optionally at an oblique angle, or optionally perpendicular with respect to the topography PCB plane 651.

In some embodiments, the first portion of an imaging axis 661 may be aligned with an axis extending along the optical tube including the illumination pattern source 640. In some embodiments, the first portion of the imaging axis 661 may be inclined at an angle with respect to the second portion of the imaging axis 662, the angle within a range from 60 to 120 degrees, optionally within a range from 80 to 100, optionally an oblique angle or optionally a perpendicular angle. In some embodiments, a second portion of the fixation axis 656 may be within a range from 25 to 65 degrees with respect to a first portion of the fixation axis 655, optionally 35 to 55 degrees, or optionally 45 degrees. In some embodiments, the second portion of the fixation axis 656 may be within a range from 45 degrees to 135 degrees with respect to a second portion of the imaging axis 661, optionally 75 degrees to 105 degrees, optionally 85 degrees to 95 degrees, optionally at an oblique angle, or optionally a perpendicular angle. In some embodiments, the second portion of the fixation axis 656 may be aligned with a first portion of the imaging axis 660.

In some embodiments, a fixation beam may extend along a fixation beam optical path or fixation axis. In some embodiments, a portion of an optical path of the imaging system may overlap with the fixation beam axis or fixation beam optical path. In some embodiments, the MCD plane and the topography PCB plane may be inclined with respect to the portion of the fixation beam optical path or fixation axis. Although the illumination pattern illustrated in many diagrams is a Placido rings, the subject matter described herein may be utilized with other illumination patterns.

In some embodiments, the imaging system of mobile communication device-based corneal topography system may include an optical configuration to adjust the image of the reflected illumination pattern being evaluated and also to decrease an optical path length between the cornea of the subject and the image sensor 625. In some embodiments, a surface of the mobile communication device 605 may be tilted with respect to a vertical axis to provide enhanced viewing of the reflected illumination pattern image by the examiner. In some embodiments, the illumination system source or component may be tilted upward with respect to a horizontal axis to facilitate alignment with an eye of a subject being examined. In some embodiments, the illumination system 640, the housing 680 and the mobile communication device 605 may be adjustable on a base to maintain a horizontal plane of alignment between a subject and an examiner during operation of the corneal topography system. In some embodiments, the mobile communication device-based corneal topography system 600 may further comprise one or more proximity sensors 820, the one or more proximity sensors coupled to the illumination system to determine whether a right eye or a left eye of the subject is being examined by detecting a cheek or a node of a subject. In some embodiments, a fixation beam may traverse a ranging beam 715 at an angle and wherein the angle is more than an angle between the MCD 605 and the topography PCB 720.

Figure 8A:
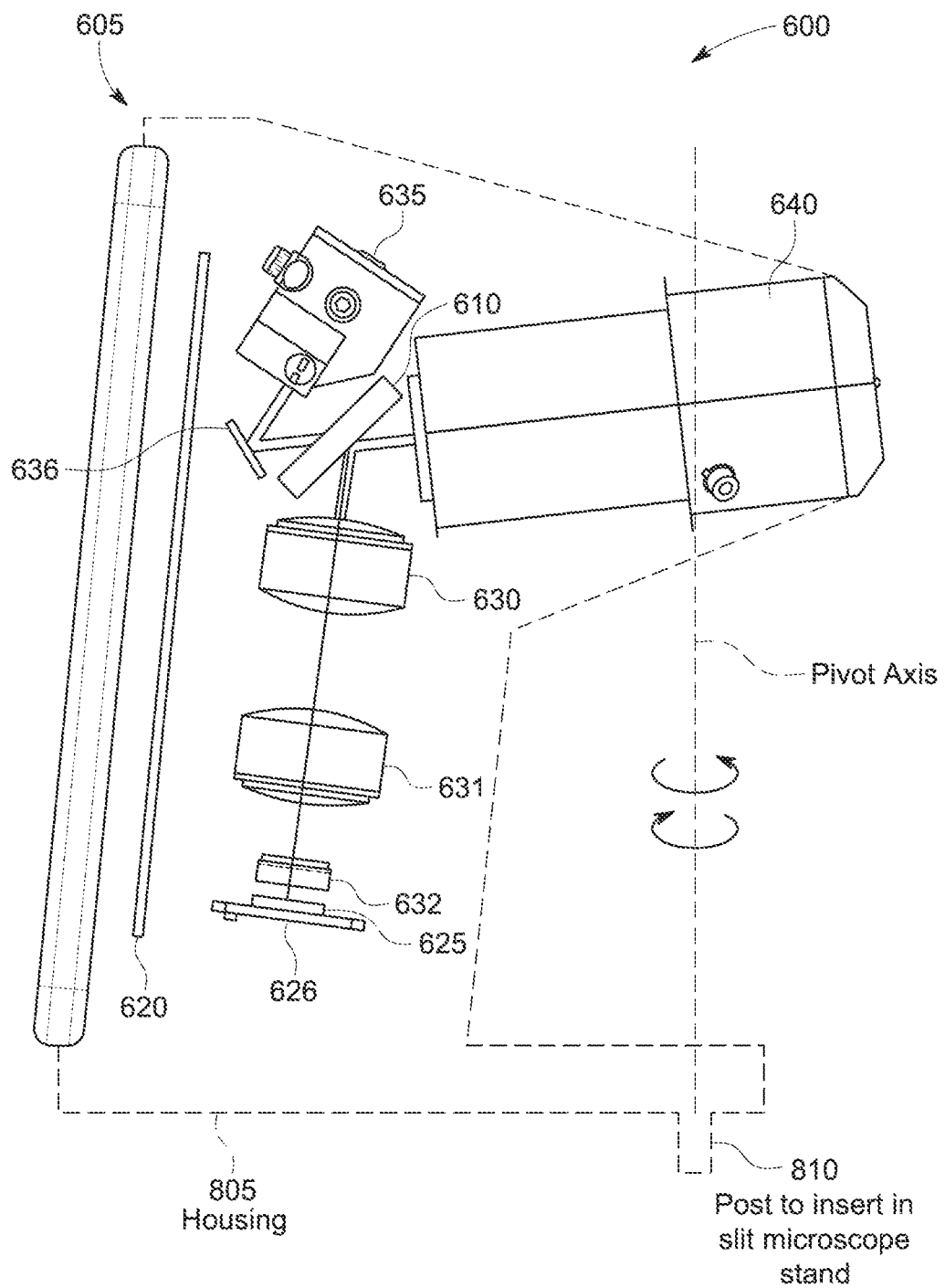
FIG. 8A illustrates that a corneal topography system may rotate about a pivot axis in order to examine both eyes of a patient according to some embodiments.
Figure 8B:
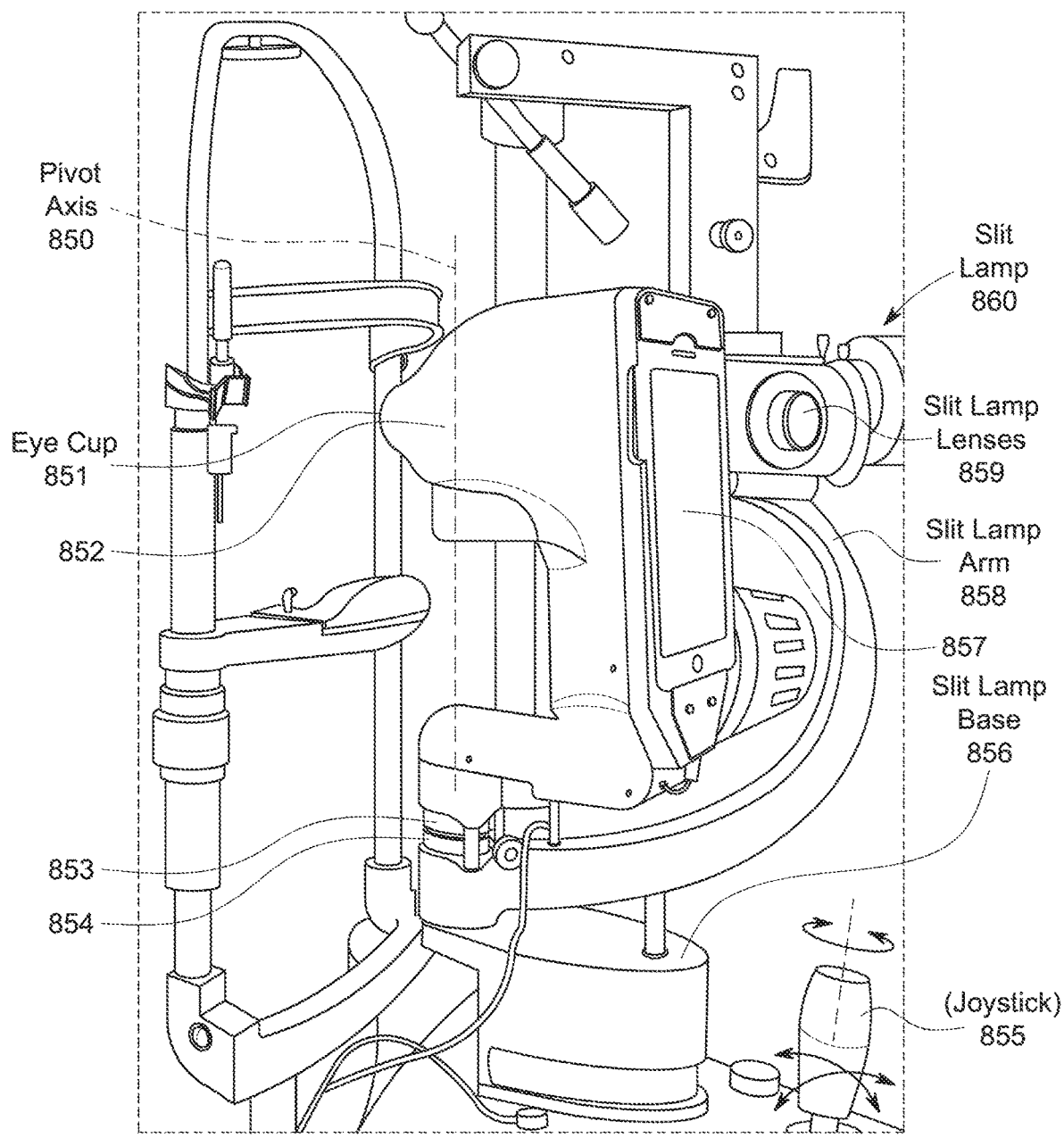
FIG. 8B illustrates a corneal topography system mounted on a slit lamp microscope according to some embodiments.

FIG. 8A illustrates that a corneal topography system as in FIG. 8 may rotate about a pivot axis in order to examine both eyes of a patient according to some embodiments. FIG. 8B illustrates the corneal topography system as in FIGS. 8 and 8A mounted on a slit lamp microscope according to some embodiments. In some embodiments, a method of operating a corneal topography system that is mounted onto a slit lamp microscope a positioning hole such as a universal positioning hole is described herein. In some embodiments, the mobile communication device-based corneal topography system, which is attached, mounted on or connected to a hole or opening in the slit-lamp microscope, does not substantially change a spatial relationship between the examiner and the patient. In other words, the examiner still feels comfortable utilizing the mobile communication device-based corneal topography system because the space between and orientation with respect to the patient and medical examiner is about the same.

In some embodiments, a positioning post as described herein may be utilized to connect to a slit lamp microscope mounting assembly. In embodiments, a mobile communication device-based corneal topography system may be attached (or piggy-backed) onto a slit-lamp microscope in order to maintain examination accuracy. With reference to FIG. 8A, in some embodiments the Z axis of the topography system comprises the optical axis of the light pattern, (e.g. the placido disk or concentric rings pattern or illumination pattern), and the optical axis of the imaging system. In embodiments, a corneal topography system may rely on +/−100 micron z-axis positional accuracy in order to have +/−0.25 Diopter accuracy in calculating accurate corneal power. In some embodiments, a mobile computing device-based corneal topography system may be attached to a slit-lamp microscope and may utilize the slit-lamp microscope's built-in and existing x-y-z positioning system, where a roller-track and a joystick provides fine motor control of x-y-z positioning. FIG. 8A illustrates a mobile-computing device-based corneal topography system configured to placed on a mounting hole within an available space of a slit lamp microscope according to some embodiments. As illustrated in FIGS. 8A and 8B, a user or examiner may utilize a joystick 855 for fine motor control of x-y-z positioning of the coupled or connected mobile computing device-based corneal topography system. In some embodiments, the joystick 855, may move the slit lamp microscope (and thus the connected mobile communication device 857 and corneal topography optical housing 852). The use of a slit-lamp microscope in the mobile computing device-based corneal topography system takes advantage of the fact that many eye care professionals are already trained in and experienced with use of a slit-lamp microscope.

In some embodiments, a corneal topography system may be picked up. In some embodiments, a support post of the corneal topography system may be placed or inserted into a positioning hole such as a universal positioning hole of a slit-lamp microscope. In some embodiments, the corneal topography system may be pivoted in a first direction in the positioning hole to align an eye cup of the corneal topography system with a first cornea of a patient. In some embodiments, the corneal topography system may capture an image of an illuminated pattern on the first cornea of the patient. In some embodiments, the corneal topography system may be pivoted in a second direction in the positioning hole to align the eye cup with a second cornea of the patient. In some embodiments, the corneal topography system may capture an image of an illuminated pattern on the second cornea of the patient. FIG. 8A illustrates a vertical pivot axis 850 running through a positioning post 810 and shows that the corneal topography system may rotate about the vertical axis in a first direction and/or a second direction. FIG. 8B illustrates a mobile communication device-based corneal topography system mounted on a slit lamp microscope In some embodiments, the slit lamp microscope may include a slit lamp 860, one or more slit lamp lenses 859, a slit lamp arm 858, a slit lamp base 856, a joystick 855, and an assembly 854 comprising a positioning hole to receive the post 810. In some embodiments, the pivot axis 850 may be a substantially vertical axis, e.g. within +/−10 degrees of vertical. In some embodiments, the mobile communication device-based corneal topography system may rotate in a left direction and/or a right direction about the pivot axis 850 in order to perform examinations on both eyes of the patient. In some embodiments, the mobile communication device-based corneal topography system may include an assembly 853 comprising positioning post 810, an eye cup 851, a housing 852 and/or a mobile communication device 857. In some embodiments assembly 853 is configured to engage assembly 854 with the post receiving in the positioning hole. Each of these assemblies may comprise a bearing surface configured to engage the other assembly when the post has been placed in the positioning hole. In some embodiments, the eye cup 851 may be on one side of the pivot axis 850 and the slim lamp lenses 859 and/or slit lamp 860 may be on another side of the pivot axis 850. In some embodiments, other components of the mobile communication device-based corneal topography system (e.g., the mobile communication device 857, an image sensor and/or portions of an imaging system) may be on an opposite side of the pivot axis 850 from the eye cup 851. In some embodiments, the eye cup 851 may be on a side of the pivot axis where the patient is located.

In some embodiments, a corneal topography system may include an illumination system configured to generate an illumination pattern reflected off a cornea of a subject, an imaging system coupled to an image sensor to capture an image of the reflected illumination pattern, a topography processor operatively coupled to the image sensor to process the image of the reflected illumination pattern and a mobile communication device. In some embodiments, the mobile communications device may includes a display, a mobile communication device processor and may be operatively coupled to the image sensor. In some embodiments, the housing at least partially enclosing one or more of the illumination system, the imaging system, or the topography processor. In some embodiments, the corneal topography system may further include a mounting or positioning post 853 coupled to the housing, the mounting post configured to be placed in a positioning hole 854 (e.g., the universal positioning hole) of a slit lamp microscope. In some embodiments, the positioning hole may include a universal positioning hole of approximately 8 mm diameter. In some embodiments, the positioning post may be configured to support the illumination system, the imaging system, the topography processor and/or the mobile communication device when placed in the universal positioning hole 854. In some embodiments, the positioning or mounting post 853 may be less than 8 mm in diameter. In some embodiments, the corneal topography housing may maintain position in the universal positioning hole 854 due to gravity. In some embodiments, the post may also maintain a position in the positioning hole via a fit of the positioning hole relative to the post (e.g., a snug fit or a tight fit), which allows the housing to maintain vertical alignment with decreased tilt and/or yaw. In some embodiments, the housing and the mounting or positioning post 853 may be configured to be able to pivot side to side about a vertical axis extending through a center of the universal positioning hole. In some embodiments, the imaging system may include an eye cup 851 where an eye is placed during examination, the eye cup 851 positioned ahead of the positioning hole 854 of the slit-lamp microscope and toward the patient relative to the positioning hole 854.

In some embodiments, the slit-lamp microscope may include lenses 859, the lenses 859 being on an opposite side of the universal positioning hole 854 from the eye cup 851. In some embodiments, the eye cup 851 may be located toward the patient relative to the positioning hole 854 and the lenses 859 of slit lamp patient may be located away from the positioning hole 854 relative to the patient. In some embodiments, the image sensor, the topography processor and the mobile communication device 857 may be positioned on the opposite side of the pivot point or axis 850 from the eye cup 851. In some embodiments, the eye cup 851 may move in an opposite direction from the image sensor, the topography processor and a display of the mobile communication device 857 when the eye cup 851 pivots about the pivot point or pivot axis 850.

In some embodiments, the corneal topography system may pivot in a range of 0.1 to 20 degrees in the first direction from a center of the universal positioning hole 854; optionally in a range of 0.1 to 40 degrees in the first horizontal direction from the center of the universal positioning hole; or optionally in a range of 0.1 to 60 degrees in the first horizontal direction from the universal positioning hole 854. In some embodiments, the corneal topography system pivots in a range of 0.1 to 20 degrees in the second direction from a center of the universal positioning hole 854; optionally in a range of 0.1 to 40 degrees in the second direction from a center of the universal positioning hole 854; or optionally in a range of 0.1 to 60 degrees in the second direction from a center of the universal positioning hole 854. In some embodiments, the first direction may be opposite the second direction. In some embodiments, the pivot in the first direction and the pivot in the second direction are about a substantially vertical axis. In some embodiments, the substantially vertical axis is within about 10 degrees of vertical.

In some embodiments, a diameter of the positioning post may be within a range of 7.5 millimeters to 8.5 millimeters; optionally may be from within a range from 7.75 mm to 8.25 mm; optionally may be within a range 7.8 millimeters to 8 millimeters; or optionally may be within a range of 7.9 millimeters to 8 millimeters.

In some embodiments, the corneal topography system may also include additional modules or subsystems in order to perform multiple diagnostic tests on a patient's eyes. This brings at least some of the benefits described including, but not limited to portability, ease of use, lower cost and the ability to reach additional patients. In other words, the housing of the mobile communication device-based corneal topography system or the corneal topography system may also include other eye or cornea diagnostic modules. In some embodiments, the corneal topography system may also include an autorefractor module to perform autorefraction on a left eye and a right eye of the patient. In some embodiments, the autorefractor module may be configured to pivot about the positioning post along with the eyecup of the corneal topography system in order to examine both the left eye and the right eye of the patient. In some embodiments, the corneal topography system may include a wavefront sensor module to identify aberrations in a left eye and a right eye of the patient. In some embodiments, the wavefront sensor module may be configured to pivot about the positioning post with the eye cup of the corneal topography system in order to examine both the left eye and the right eye of the patient. In some embodiments, the corneal topography system may include a fundus camera module to capture an image of a retina of a patient's left eye and right eye. In some embodiments, the fundus camera may be configured to pivot about the positioning post with the eyecup of the corneal topography system in order to examine both the left eye and the right eye of the patient. In some embodiments, the corneal topography system may include a Scheimpflug camera or corneal tomography module to capture images of a cornea of a patient's left eye and right eye. In some embodiments, the Scheimpflug camera or corneal tomography module may be configured to pivot about the positioning post with the eyecup of the corneal topography system in order to examine both the left eye and the right eye of the patient. In some embodiments, the corneal topography system may include a laser interferometer module to capture intraocular lens (IOL) power calculations of a patient's left eye and a right eye. In some embodiments, the laser interferometer may be configured to pivot about the positioning post with the eyecup of the corneal topography system in order to examine both the left eye and the right eye of the patient.

In some embodiments, other modules or systems may be placed into the positioning hole of the slit lamp microscope like the corneal topography system described herein and/or may have mobile communication devices mounted to surfaces thereof. This allows an eye doctor to be able to utilize the slit lamp microscope to perform a number of eye examinations without having to purchase additional special equipment. In some embodiments, after the corneal topography system has performed diagnostic examinations of the right eye and the left eye, the corneal topography system may be removed from the positioning hole of the slit lamp microscope. In some embodiments, a mobile communication device-based autorefractor system, a mobile communication device-based corneal tomography system, a mobile communication device-based Scheimpflug system, a mobile communication device-based wavefront sensor system, a mobile communication device-based fundus camera system, and/or a mobile communication device-based laser interferometer system may be lifted. In some embodiments, a mounting post of the mobile communication device-based autorefractor system, the mobile communication device-based corneal tomography system, the mobile communication device-based wavefront sensor system, a mobile communication device-based Scheimpflug system, the mobile communication device-based fundus camera system, or the mobile communication device-based laser interferometer system may be placed in the universal positioning hole of the slit lamp microscope in order for examinations to be performed on the patient's left eye and the right eye. In some embodiments, this may continue for multiple mobile-communication device eye examination systems that utilize the same platform for mounting and thus can be easily removed if a different examination is requested.

In some embodiments, a topography processor may be configured to generate topography data and derived topography data. In some embodiments, the mobile communication device to communicate the generated topography data and the derived topography data to a cloud-based computing device. In some embodiments, the mobile communication device to communicate the image of the reflected illumination pattern to the cloud-based computing device. In some embodiments, the examiner looks down at an angle from horizontal within a range of 2.5 degrees to 15 degrees towards a display of the mobile communication device in the mobile communication device-corneal topography system, or optionally within a range of 5 degrees to 10 degrees towards a display of the mobile communication device.

In some embodiments, the eye cup 851 may be located toward the patient from the mounting post to allow an angle of the eye cup 851 to change in response to anatomical differences between a left eye and a right eye of a patient. In some embodiments, the slit lamp microscope may include a slit lamp base, the slit lamp base 856 coupled to the hole and lenses of the slit lamp. In some embodiments, the slit lamp base 856 includes a joy stick 855 configured to translate the hole of the slit lamp along two directions with pivoting of the joy stick along two corresponding directions and wherein rotation of the joystick about an elongate axis of the joystick raises or lowers the hole of the slit lamp microscope.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Referrals to instructions refers to computer-readable instructions executable by one or more processors in order to perform functions or actions. The instructions may be stored on computer-readable mediums and/or other memory devices. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

As used herein, the term "or" is used inclusively to refer items in the alternative and in combination.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A corneal topography system for measuring topography of a cornea of an eye, the system comprising:
    an illumination pattern to reflect light from the cornea;
    a fixation beam, the fixation beam comprising a first wavelength of light;
    an alignment beam focused at a location overlapping with the fixation beam, the alignment beam comprising a second wavelength of light different from the first wavelength of light;
    a detector to image a reflection of the fixation beam from the cornea and scattered light from the alignment beam illuminating the cornea; and
    a processor coupled to the detector, the processor configured with instructions to:
    display an image of the eye showing the reflection of the fixation beam and the scattered light from the alignment beam illuminating the cornea; and
    capture an image of the illumination pattern in response to the fixation beam overlapping with the scattered light from the alignment beam.

2. The corneal topography system of claim 1, wherein the alignment beam is focused near a vertex of the cornea when the scattered light from the alignment beam overlaps with the reflection of the fixation beam in the image.

3. The corneal topography system of claim 1, wherein the image of the eye shows the reflection of the fixation beam overlapping with the scattered light from the alignment beam and the image of the illumination pattern is captured in response to the image of the eye.

4. The corneal topography system of claim 1, wherein a distance across the alignment beam illuminating the cornea is within a range of 5 microns to 200 microns, optionally within a range of 10 microns to 150 microns, or optionally within a range of 20 microns to 100 microns.

5. The corneal topography system of claim 1, wherein the image of the eye comprises a Purkinje image of the fixation beam and wherein a distance across the fixation beam in the Purkinje image of the eye is within a range of 10 microns to 300 microns, optionally within a range of 25 microns to 200 microns, or optionally within a range of 50 to 150 microns.

6. The corneal topography system of claim 1, wherein a reticle is displayed on the mobile communication device screen when the scattered light overlaps the reflection of the fixation beam and wherein the overlapping area of the beams in the image corresponds to a distance across the cornea within a range of 10 microns to 200 microns, optionally a range of 15 microns to 125 microns, or optionally a range of 20 microns to 75 microns.

7. The corneal topography system of claim 1, wherein the image of the illumination pattern comprises an innermost concentric ring having a diameter larger than one or more of a distance across the reflection of the fixation beam or a distance across the alignment beam.

8. The corneal topography system of claim 1, wherein the image of the illumination pattern comprises a Purkinje image of the illumination pattern and the reflection of the fixation beam comprises a Purkinje image of the fixation beam.

9. The corneal topography system of claim 8, wherein the Purkinje image of the illumination pattern is located farther from a vertex of the cornea than the Purkinje image of the fixation beam.

10. The corneal topography system of claim 1, wherein the scattered light from the alignment beam illuminating the cornea originates from the cornea.

11. The corneal topography system of claim 1, wherein a camera coupled to the detector comprises a depth of field sufficient to image a Purkinje image of the illumination pattern, a Purkinje image of the reflection of the fixation beam and the scattered light from the alignment beam.

12. The corneal topography system of claim 1, wherein the illumination system comprises a Placido ring assembly including a plurality of concentric rings, wherein the plurality of concentric rings is formed by a geometry of a Placido ring component, and the Placido ring component is illuminated by a plurality of light-emitting diodes (LEDs).

13. The corneal topography system of claim 1, wherein a luminescence intensity of the pattern at the cornea is within a range from 10 lux to 500 lux, optionally from 25 lux to 250 lux, or optionally from 50 lux to 125 lux.

14. The corneal topography system of claim 1, wherein the illumination pattern comprises a third wavelength of light, the third wavelength of light different from the first wavelength of light and the second wavelength of light.

15. The corneal topography system of claim 1, wherein the eye of a patient looks downward from horizontal at an angle within a range of 2.5 degrees to 15 degrees towards the fixation beam, or optionally looks downward within a range of 5 degrees to 10 degrees towards the fixation beam, or optionally where the eye of the patient and the fixation beam are substantially horizontal with respect to each other.

16. The corneal topography system of claim 1, wherein the alignment beam is inclined in the horizontal plane relative to an optical axis and the fixation beam, and focused to a cross-sectional size on the cornea to position the vertex of the cornea along the optical axis with an error of no more than 150 microns when the fixation beam overlaps with the alignment beam in the image of the eye, and optionally wherein the error is no more than 100 microns, optionally no more than 50 microns and optionally no more than 25 microns.

17. A mobile communication device-based corneal topography system, comprising:
a mobile communication device comprising a mobile communication device (MCD) processor and a display;
a fixation beam source to generate a fixation beam and direct the fixation beam to the cornea of the subject, the fixation beam defining a fixation target visible to the eye of the subject, the fixation target beam comprising a first wavelength of light;
a ranging beam source to generate a ranging beam and direct the ranging beam to a cornea of a subject, the ranging beam comprising a second wavelength of light different from the first wavelength of light;
an imaging system coupled to an image sensor to capture a reflected image of the ranging beam and the fixation beam on the cornea; and
a topography processor operatively coupled to the image sensor and configured with instructions to:
determine when the ranging beam and the fixation beam are overlapping by tracking the first wavelength of light and the second wavelength of light with spectral analysis and determining the fixation beam and the ranging beam are aligned with a mark in a center of the reflected image;
turn off the ranging beam source and the fixation beam source;
automatically capture, at the image sensor, an image of a reflected illumination pattern reflected off the cornea of the subject;
transmit the captured image of the reflected illumination pattern to the topography processor; and
process, by the topography processor, the image of the reflected illumination pattern to generate one or more topography map images and one or more topography data files.

18. The mobile communication device-based corneal topography system of claim 17, the topography processor configured with instructions to communicate the one or more topography map images and the one or more topography data files to the mobile communication device.

19. The mobile communication device-based corneal topography system of claim 18, the MCD processor configured with instructions to present the one or more topography map images on the mobile communication device display.

20. A method to automatically capture a reflected Placido rings image of a patient's cornea comprising:
activating a ranging light source to generate a ranging light beam having a first color and a fixation light source to generate a fixation light beam having a second color;
adjusting a position of a camera with respect to the patient's cornea;
detecting a presence of a scatter beam having a third color in a video image of the patient's cornea, the scatter beam identifying an overlapping of the ranging beam with the fixation beam in the video image, wherein the third color is an additive result of the first color and the second color;
deactivating the ranging beam;
illuminating a Placido rings assembly to cause a reflection of a Placido rings image on the patient's cornea; and
automatically capturing the reflected Placido rings image.

* * * * *